(12) United States Patent
Schumacher et al.

(10) Patent No.: US 7,087,625 B2
(45) Date of Patent: Aug. 8, 2006

(54) PHOSPHODIESTERASE 4 INHIBITORS

(75) Inventors: Richard A. Schumacher, Monroe, NY (US); Elizabeth Doorly Graham, River Vale, NJ (US); Allen T. Hopper, Glen Rock, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 68 days.

(21) Appl. No.: 10/715,819

(22) Filed: Nov. 19, 2003

(65) Prior Publication Data

US 2004/0152902 A1  Aug. 5, 2004

Related U.S. Application Data

(60) Provisional application No. 60/427,221, filed on Nov. 19, 2002.

(51) Int. Cl.
C07D 213/02 (2006.01)
C07D 419/12 (2006.01)
A61K 31/44 (2006.01)

(52) U.S. Cl. ............ 514/337; 514/338; 514/357; 546/275.7; 546/283.4; 546/546; 546/334

(58) Field of Classification Search ............ 514/337, 514/338, 357; 546/275.7, 283.4, 334
See application file for complete search history.

(56) References Cited

U.S. PATENT DOCUMENTS

| | | | |
|---|---|---|---|
| 5,591,776 A | 1/1997 | Cavalla et al. |
| 5,622,977 A | 4/1997 | Warrellow et al. |
| 5,633,257 A | 5/1997 | Warrellow et al. |
| 5,679,696 A | 10/1997 | Fenton et al. |
| 5,693,659 A | 12/1997 | Head et al. |
| 5,698,711 A | 12/1997 | Palfreyman |
| 5,710,160 A | 1/1998 | Guay et al. |
| 5,710,170 A | 1/1998 | Guay et al. |
| 5,712,298 A | 1/1998 | Amschler |
| 5,723,460 A | 3/1998 | Warrellow et al. |
| 5,728,712 A | 3/1998 | Montana et al. |
| 5,739,144 A | 4/1998 | Warrellow et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow et al. |
| 5,814,651 A | 9/1998 | Duplantier et al. |
| 5,840,724 A | 11/1998 | Fenton et al. |
| 5,849,770 A | 12/1998 | Head et al. |
| 5,859,034 A | 1/1999 | Warrellow et al. |
| 5,866,593 A | 2/1999 | Warrellow et al. |
| 5,880,135 A | 3/1999 | Gully et al. |
| 5,889,014 A | 3/1999 | Cavalla et al. |
| 5,891,896 A | 4/1999 | Warrellow et al. |
| 5,919,937 A | 7/1999 | Lynch et al. |
| 5,935,978 A | 8/1999 | Fenton et al. |
| 5,962,483 A | 10/1999 | Warrellow et al. |
| 5,962,492 A | 10/1999 | Warrellow et al. |
| 6,040,329 A | 3/2000 | Marfat |
| 6,077,854 A | 6/2000 | Warrellow et al. |
| 6,096,768 A | 8/2000 | Ashton et al. |

(Continued)

FOREIGN PATENT DOCUMENTS

EP   0994100 A1   4/2000

(Continued)

OTHER PUBLICATIONS

Heilman et al, "Synthesis and Antiinflammatory Evaluation of Substitued Isophthalonitriles, Trimesonitriles, Benzonitriles,and Terephthalonitriles", Journal of Medicinal Chemistry, 1978, vol. 21, No. 9, pp. 906-913, XP-002226236.

(Continued)

Primary Examiner—Zinna N. Davis
(74) Attorney, Agent, or Firm—Millen, White, Zelano, Branigan, P.C.

(57) ABSTRACT

PDE4 inhibition is achieved by novel nitroxide compounds, e.g., N-substituted aniline and diphenylamine analogs. The compounds of the present invention are of Formulas I–III:

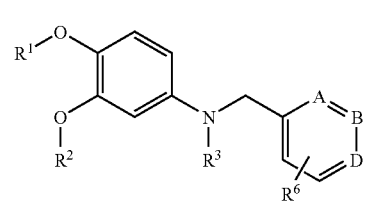

I

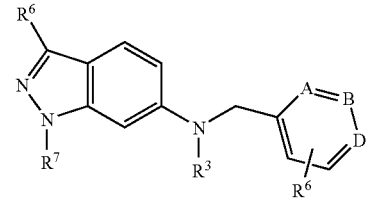

II

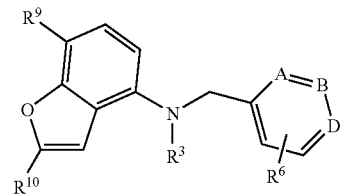

III wherein A, B, D, $R^1$, $R^2$, $R^3$, $R^7$, $R^8$, $R^9$, $R^{10}$ and $R^6$ are as defined herein.

84 Claims, No Drawings

U.S. PATENT DOCUMENTS

| | | | |
|---|---|---|---|
| 6,153,630 | A | 11/2000 | Cavalla et al. |
| 6,162,830 | A | 12/2000 | Connor et al. |
| 6,180,650 | B1 | 1/2001 | Frenette et al. |
| 6,200,993 | B1 | 3/2001 | Cote et al. |
| 6,204,275 | B1 | 3/2001 | Friesen et al. |
| 6,245,774 | B1 | 6/2001 | Warrellow et al. |
| 6,255,326 | B1 | 7/2001 | Ashton et al. |
| 6,262,040 | B1 | 7/2001 | Marfat |
| 6,297,264 | B1 | 10/2001 | Head et al. |
| 2002/0151566 | A1 | 10/2002 | Schumacher et al. |

FOREIGN PATENT DOCUMENTS

| | | |
|---|---|---|
| EP | 1116711 A2 | 7/2001 |
| FR | 2729142 A1 | 7/1996 |
| JP | 11-189577 | 7/1999 |
| JP | 2001 11047 | 1/2001 |
| WO | WO 93/25517 | 12/1993 |
| WO | WO 94/02465 | 2/1994 |
| WO | WO 94/14742 | 7/1994 |
| WO | WO 94/27971 A1 | 12/1994 |
| WO | WO 95/01338 | 1/1995 |
| WO | WO 95/04046 | 2/1995 |
| WO | WO 95/20578 | 8/1995 |
| WO | WO 96 21435 | 7/1996 |
| WO | WO 96/21435 A1 | 7/1996 |
| WO | WO 96/23754 | 8/1996 |
| WO | WO 96/36620 | 11/1996 |
| WO | WO 97 00868 | 1/1997 |
| WO | WO 97 49702 | 12/1997 |
| WO | WO 98 09961 | 3/1998 |
| WO | WO 98/58901 | 12/1998 |
| WO | WO 99/33806 | 7/1999 |
| WO | WO 00/50402 | 8/2000 |
| WO | WO 00/64874 | 11/2000 |
| WO | WO 00 69841 | 11/2000 |
| WO | WO 00/71129 A1 | 11/2000 |
| WO | WO 01/70738 | 9/2001 |
| WO | WO 02 059110 | 8/2002 |
| WO | WO 02/074726 | 9/2002 |
| WO | WO 02 074726 | 9/2002 |
| WO | WO 2004/009552 | 1/2004 |

OTHER PUBLICATIONS

Watanabe et al, "Structure-Activity Relationship and Rational Design of 3,4-Dephostatin Derivatives as Protein Tyrosine Phosphatase Inhibitors", Pergamon Tetrahedron, 2000, vol. 56, pp. 741-752.

Inoue et al, "Steric Tuning in Chiral Ligand Mediated Enantioselective Alkylation of Imines", Tetrahedron: Asymmetry, 1993, vol. 4, No. 7, pp. 1603-1606, XP002226237.

Thomas C. McKenzie et al., "The Gomberg-Bachmann Reaction of Purines", *J. Heterocyclic Chem.*, May-Jun. 1987, pp. 859-861, vol. 24.

Vasu Nair et al., "Novel, Stable Congeners of Antiretroviral Compound 2', 3'- Dideoxyadenosine," *J. Am. Chem. Soc.*, 1989, pp. 8502-8504, vol. 111.

Vasu Nair et al., "Synthesis Of Congeners Of Adenosine Resistant To Deamination By Adenosine Deaminase," *J. Chem. Soc Comm.*, 1989, pp. 878-879.

James L. Kelley et al., "Synthesis and Structure- Activity Relationships of 2-Substituted-6-(dimethylamino)- 9-(4-methylbenzyl)-9H-purines with Antirhinovirus Activity," *J. Med. Chem.*, 1989, pp. 218-224, vol. 32.

James E. Kelley et al., "Antirhinovirus structure-activity relationships of 6-substituted-9-(4-methylbenzyl)-2-trifluoromethyl-9H-purines," *Eur. J. Med. Chem.*, 1990, pp. 131-135, vol. 25.

Roger J. Schilling et al., "A High-Throughput Assay For Cyclic Nucleotide Phosphodiesterases," *Analytical Biochemistry*, 1994, pp. 154-158, vol. 215.

Donald V. Daniels et al., "A Semiautomated Method for the Assay of Cyclic Adenosine 5'- Monophosphate Phosphodiesterase," *Analytical Biochemistry*, 1996, pp. 367-369, vol. 236.

Jean-Jacques Bourguignon et al., "9-Benzyladenines: Potent and Selective cAMP Phosphodiesterase Inhibitors," *J. Med. Chem*, 1997, pp. 1768-1770, vol. 40.

James L. Kelley et al., "6-(Alkylamino)-9-alkylpurines. A New Class of Potential Antipsychotic Agents," *J. Med. Chem.*, 1997, pp. 3207-3216, vol. 40.

Hiroyuki Sawanishi et al., "Selective Inhibitors of Cyclic AMP-Specific Phosphodiesterase: Heterocycle-Condensed Purines", *J. Med. Chem.*, 1997, pp. 3248-3253, vol. 40.

J.E. Sounnes et al., "Proposal for Pharmacologically Distinct Conformers of PDE4 Cyclic AMP Phosphodiesterase", *Cell Signal*, 1997, pp. 227-236. vol. 9, No. 3-4.

Mary Elizabeth Bach et al., "Age-related defects in spatial memory are correlated with defects in the late phase of hippocampal long term potentiation in vitro and are attenuated by drugs that enhance the cAMP signaling pathway", *Proc. Natl. Acad. Sci. USA*, Apr. 1999, pp. 5280-5285, vol. 96.

Elisabeth Boichot et al., "Anti-Inflammatory Activities of a New Series of Selective Phosphodiesterase 4 Inhibitors Derived from 9- Benzyladenine," *The Journal Of Pharmacology And Experimental Therapeutics*, 2000, pp. 647-653, vol. 292, No. 2.

Anil S. Guram et al., "A Simple Catalytic Method for the conversion of Aryl Bromides to Arylamines," Angew. Chem. Int, Ed. Engl., 1995, vol. 34, No. 12, pp. 1348-1350.

Michael S. Driver et al., "A Second-Generation Catalyst for the Aryl Halide Amination: Mixed Secondary Amines from Aryl Halides and Primary Amines Catalyzed by $(DPPF)PdCI_2$," J. Am. Chem. Soc., 1996, vol. 118, pp. 7217-7218.

Takashi Egawa et al., "Rolipram and its Optical Isomers, Phosphodiesterase 4 Inhibitors, Attenuated the Scopolamine-Induced Impairments of Learning and Memory in Rats," J. Pharmacol., vol. 75, 275-281(1997).

Peng Wang et al., "Expression, Purification, and Characterization of Human cAMP-Specific Phosphodiesterase (PDE4) Subtypes A, B, C, and D,"Biochem. And Biophys. Research Comm., vol. 234, 320-324 (1997).

Domine M. T. Chan et al., "New N- abd O-Arylations with Phenylboronic Acids and Cupric Acetate," Tetrahedron Letters, vol. 39, 2933-2936 (1998).

Mark Barad et al., "Rolipram, a Type IV-Specific Phosphodiesterase Inhibitor Facilitates the Establishment of Long-lasting Long-term Potentiation and Improves Memory," Proc. Natl. Acad. Sci., vol. 95, pp. 15020-15025 (Dec. 1998).

Miles D. Houslay et al., "The Multienzyme PDE4 Cyclic Adenosine Monophosphate-Specific Phosphodiesterase Family: Intracellular Targeting, Regulation, and Selective Inhibition by Compounds Exerting Anti-inflammatory and Antidepressant Actions," *Advances in Pharmacology*, vol. 44, pp. 225-342, 1998.

John Hartwig et al., "Room-Temperature Palladium-Catalyzed Amination of Aryl Bromides and Chlorides and Extended Scope of Aromatic C-N Bond Formation with a Commercial Ligand," J. Org. Chem., 1999, vol. 64, pp. 5575-5580.

Han-Ting Zhang et al., "Inhibition of Cyclic AMP Phosphodiesterase (PDE4) Reverses Memory Deficits Associated with NDMA Receptor Antagonism," Neuropsychopharmacology, 2000, vol. 23, pp. 198-204.

Han-Ting Zhang et al., "Effects of Rolipram on Scopolamine-induced Impairment of Working and Reference Memory in the Radial-arm Maze tests in Rats," Psychopharmacology (Berl) Jun. 2000;150(3):pp. 311-316.

T.W. Greene et al., *Protective Groups in Organic Synthesis*, 3rd Edition, Chapter 3, "Protection for Phenols and Catechols," pp. 246-292, John Wiley & Sons, 1999.

Japanese Patent Abstract No. 7206789 dated Aug. 8, 1995.

T. J. Martin, "PDE4 Inhibitors—A Review of the Recent Patent Literature", IDRUGS, Current Drugs Ltd., vol. 4, No. 3, (2001), pp. 312-338.

PCT Written Opinion dated Jan. 28, 2005.

International Search Report dated Jan. 19, 2005.

PHOSPHODIESTERASE 4 INHIBITORS

This application claims the benefit of priority of U.S. provisional application No. 60/427,221, filed Nov. 19, 2002, the entire disclosure of which is hereby incorporated by reference.

FIELD OF THE INVENTION

The present invention relates generally to the field of phosphodiesterase 4 (PDE4) enzyme inhibition. More specifically this invention relates to selective PDE4 inhibition by novel compounds, e.g., pyridine N-oxide analogs of N-substituted diarylamines, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.*, 234, 320–324 (1997)]. In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

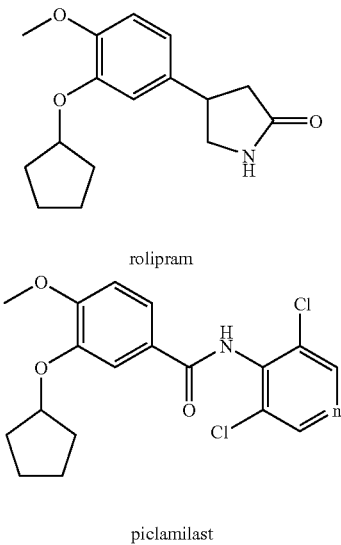

rolipram piclamilast

In addition to such compounds as rolipram, xanthine derivatives such as pentoxifylline, denbufylline, and theophylline inhibit PDE4 and have received considerable attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an anti-depressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799–807 for a general review). Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion and stomach erosion.

SUMMARY OF THE INVENTION

The present invention relates to novel compounds, e.g., pyridine N-oxide analogs of N-substituted diarylamine compounds, that inhibit PDE4 enzymes, and especially have improved side effect profiles, e.g., are relatively non-emetic, (e.g., as compared to the previously discussed prior art compounds). Preferably, the compounds selectively inhibit PDE4 enzymes. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, requiring PDE inhibition, especially PDE4 inhibition, for a disease state that involves elevated intracellular PDE 4 levels or decreased cAMP levels, e.g., involving neurological syndromes, especially those states associated with memory impairment, most especially long term memory impairment, as where such memory impairment is due in part to catabolism of intracellular cAMP levels by PDE 4 enzymes, or where such memory impairment may be improved by effectively inhibiting PDE4 enzyme activity.

In a preferred aspect, the compounds of the invention improve such diseases by inhibiting PDE4 enzymes at doses which do not induce emesis.

The present invention includes nitroxide compounds of Formulas I–III:

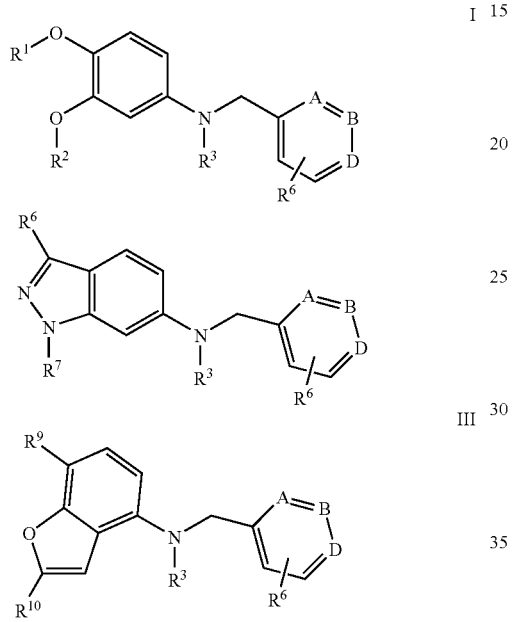

wherein
one of A, B and D is N—O and the others are $CR^6$ (preferably, B is N—O)

$R^1$ is alkyl having 1 to 4 carbon atoms, which is branched or unbranched and which is unsubstituted or substituted one or more times by halogen (e.g., $CH_3$, $CHF_2$, $CF_3$, etc.);

$R^2$ is alkyl having 1 to 12, preferably 1 to 8 carbon atoms, which is branched or unbranched and which is unsubstituted or substituted one or more times by halogen, hydroxy, cyano, $C_{1-4}$-alkoxy, oxo or combinations thereof, and wherein optionally one or more —$CH_2CH_2$— groups is replaced in each case by —CH=CH— or —C≡C— (e.g., $CH_3$, $CHF_2$, $CF_3$, methoxyethyl, etc.),
  cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
  cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof (e.g., cyclopentylmethyl, cyclopropylmethyl, etc.),
  aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, cyano, or combinations thereof (e.g., methylphenyl, methoxyphenyl, chlorophenyl, etc.),
  arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, $CF_3$, $OCF_3$, alkyl, hydroxy, alkoxy, nitro, cyano, methylenedioxy, ethylenedioxy, or combinations thereof, and wherein in the alkyl portion one or more —$CH_2CH_2$— groups are each optionally replaced by —CH=CH— or —C≡C—, and/or one or more —$CH_2$— groups are each optionally replaced by —O— or —NH— and/or the alkyl portion is optionally substituted by halogen, oxo, hydroxy, cyano, or combinations thereof (e.g., phenylethyl, phenylpropyl, phenylbutyl, methoxyphenylethyl, methoxyphenylpropyl, chlorophenylethyl, chlorophenylpropyl, phenylethenyl, phenoxyethyl, phenoxybutyl, chlorophenoxyethyl, chlorophenylaminoethyl, etc.),
  a partially unsaturated carbocyclic group having 5 to 14 carbon atoms, which is unsubstituted or substituted one or more times by halogen, alkyl, alkoxy, hydroxy, nitro, cyano, oxo, or combinations thereof (e.g., cyclohexenyl, cyclohexadienyl, indanyl, tetrahydronaphthenyl, etc.),
  a heterocyclic group, which is saturated, partially saturated or unsaturated, having 5 to 10 ring atoms in which at least 1 ring atom is an N, O or S atom, wherein the heterocyclic group is unsubstituted or substituted one or more times by halogen, hydroxy, aryl, alkyl, alkoxy, cyano, trifluoromethyl, nitro, oxo, or combinations thereof (e.g., 3-thienyl, 3-tetrahydrofuranyl, 3-pyrrolyl, etc.), or
  a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted or substituted one or more times in the heterocyclic portion by halogen, $OCF_3$, hydroxy, aryl, alkyl, alkoxy, cyano, trifluoromethyl, nitro, oxo, or combinations thereof, wherein in the alkyl portion one or more —$CH_2CH_2$— groups are each optionally replaced by —CH=CH— or —C≡C—, and/or one or more —$CH_2$— groups are each optionally replaced by —O— or —NH— and/or the alkyl portion is optionally substituted by halogen, oxo, hydroxy, cyano, or combinations thereof (e.g., pyridylethyl, pydridylpropyl, methylpiperazinylethyl, etc.);

$R^3$ is H,
  cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
  aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, OCF$_3$, amino, aminoalkyl, aminoalkoxy dialkylamino, hydroxyalkyl (e.g., hydroxymethyl), hydroxamic acid, pyrrolyl, tetrazole-5-yl, 2(-heterocycle)tetrazole-5-yl (e.g., 2-(2-tetrahydropyranyl)tetrazole-5-yl), hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (e.g. tert-butyldimethylsilyloxy), R$^4$-L-, or combinations thereof (e.g., substituted or unsubstituted phenyl, naphthyl, and biphenyl, such as phenyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), heteroaryl having 5 to 10 ring atoms in which at least 1 ring atom is a heteroatom (preferably N, S or O), which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (e.g., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (e.g. tert-butyldimethylsilyloxy), R$^4$-L-, or combinations thereof (e.g., pyridyl, thienyl, pyrazinyl, quinolinyl, isoquinolinyl, pyrimidinyl, imidazolyl, thiazolyl, etc.), or a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, trifluoromethyl, nitro, oxo, or combinations thereof (e.g., 3-thienyl, 3-tetrahydrofuranyl, 3-pyrrolyl, etc.);

R$^4$ is H, alkyl having 1 to 8, preferably 1 to 4 carbon atoms, which is unsubstituted or substituted one or more times by halogen, C$_{1-4}$-alkyl, C$_{1-4}$-alkoxy, oxo, or combinations thereof (e.g., methyl, ethyl, propyl, etc.), alkylamino or dialkylamino wherein each alkyl portion has independently 1 to 8, preferably 1 to 4 carbon atoms (e.g., dimethylamino, etc.), a partially unsaturated carbocycle-alkyl group wherein the carbocyclic portion has 5 to 14 carbon atoms and the alkyl portion has 1 to 5 carbon atoms, which is unsubstituted or substituted, preferably in the carbocyclic portion, one or more times by halogen, alkyl, alkoxy, nitro, cyano, oxo, or combinations thereof (e.g., cyclohexenylmethyl, etc.), cycloalkyl having 3 to 10, preferably 3 to 8 carbon atoms, which is unsubstituted or substituted one or more times by halogen, hydroxy, oxo, cyano, alkoxy, alkyl having 1 to 4 carbon atoms, or combinations thereof (e.g., cyclopentyl), cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, alkyl, alkoxy or combinations thereof (e.g., cyclopentylmethyl, cyclopropylmethyl, etc.), aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy, dialkylamino, hydroxyalkyl (e.g., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, cycloalkyl, aryl (e.g., phenyl, naphthyl, and biphenyl), heteroaryl, or combinations thereof (e.g., substituted or unsubstituted phenyl and naphthyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH=CH— or —C≡C—, and/or one or more —CH$_2$— groups are each optionally replaced by —O— or —NH— (e.g., benzyl, phenethyl, phenpropyl, methylbenzyl, methoxybenzyl, trfluoromethyl, benzyl, methylenedioxobenzyl, etc.), a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (e.g., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, or combinations thereof (e.g., pyridyl, thienyl, pyrazinyl, quinolinyl, isoquinolinyl, pyrimidinyl, imidazolyl, thiazolyl, etc.), or a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, CF$_3$O, nitro, oxo, amino, alkylamino, dialkylamino, or combinations thereof and/or substituted in the alkyl portion by halogen, cyano, or methyl or combinations thereof (e.g., pyridylmethyl, pyridylpropyl, methylpridylmethyl, etc.);

L is a single bond or a divalent aliphatic radical having 1 to 8 carbon atoms wherein one or more —CH$_2$— groups are each optionally replaced by —O—, —S—, —SO—, —SO$_2$—, —NR$^5$—, —SO$_2$NH—, —NHSO$_2$—, —SO$_2$NR$^5$—, —NR$^5$SO$_2$—, —CO—, —NR$^5$CO—, —CONR$^5$—, —NHCONH—, —OCONH—, —NHCOO—, —SCONH—, —SCSNH—, or —NHCSNH— (e.g., —O—, —CH$_2$—, —CO—, —CO—O—, —O—CO—, —CO—NH—, —NH—CO—, —CH$_2$CH$_2$CH$_2$—NH—CO—, —CH$_2$—CH$_2$—O—, —SO$_2$—NH—CH$_2$CH$_2$—O—, —O—CH$_2$CH$_2$—O—, —CH$_2$—NH—CO—, —CO—NH—CH$_2$—, —SO$_2$—NH—, —CH$_2$—NH—SO$_2$—, —CH$_2$CH$_2$CH$_2$—SO$_2$—NH—, —CO—NH—SO$_2$—, —SO$_2$—, —SO$_2$NHCO—, etc.);

R$^5$ is H,
  alkyl having 1 to 8, preferably 1 to 4 carbon atoms, which is branched or unbranched and which is unsubstituted or substituted one or more times by halogen, C$_{1-4}$-alkyl, C$_{1-4}$-alkoxy, oxo, or combinations thereof (e.g., methyl, ethyl, propyl, etc.),
  aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (e.g., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, (e.g., substituted or unsubstituted phenyl and naphthyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), or
  arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH=CH— or —C≡C—, and/or one or more —CH$_2$— groups are each optionally replaced by —O— or —NH— (e.g., benzyl, phenethyl, phenpropyl, methylbenzyl, methoxybenzyl, trfluoromethyl, benzyl, methylenedioxobenzyl, etc.);

R$^6$ is H, halogen, alkyl having 1 to 4 carbon atoms, alkoxy having 1 to 4 carbon atoms, CN, or hydroxyl;

R$^7$ is H,
  alkyl having 1 to 8 carbon atoms, which is branched or unbranched and which is unsubstituted or substituted one or more times by halogen, cyano, hydroxy, C$_{1-4}$-alkoxy, or combinations thereof
  cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
  cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, C$_{1-4}$-alkyl, C$_{1-4}$-alkoxy or combinations thereof (e.g., cyclopentylmethyl, cyclopropylmethyl, etc.),
  aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, cyano, or combinations thereof (e.g., methylphenyl, methoxyphenyl, chlorophenyl, etc.),
  arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, CF$_3$, OCF$_3$, alkyl, hydroxy, alkoxy, nitro, cyano, methylenedioxy, ethylenedioxy, or combinations thereof, and wherein in the alkyl portion one or more —CH$_2$CH$_2$— groups are each optionally replaced by —CH=CH— or —C≡C—, and/or one or more —CH$_2$— groups are each optionally replaced by —O— or —NH— and/or the alkyl portion is optionally substituted by halogen, oxo, hydroxy, cyano, or combinations thereof (e.g., phenylethyl, phenylpropyl, phenylbutyl, methoxyphenylethyl, methoxyphenylpropyl, chlorophenylethyl, chlorophenylpropyl, phenylethenyl, phenoxyethyl, phenoxybutyl, chlorophenoxyethyl, chlorophenylaminoethyl, etc.),
  a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (e.g., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, or combinations thereof (e.g., tetrahydrofuranyl, pyridyl, thienyl, pyrazinyl, quinolinyl, isoquinolinyl, pyrimidinyl, imidazolyl, thiazolyl, etc.), or
  a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted or substituted one or more times in the heterocyclic portion by halogen, OCF$_3$, hydroxy, aryl, alkyl, alkoxy, cyano, trifluoromethyl, nitro, oxo, or combinations thereof, wherein in the alkyl portion one or more —CH$_2$CH$_2$— groups are each optionally replaced by —CH=CH— or —C≡C—, and/or one or more —CH$_2$— groups are each optionally replaced by —O— or —NH— and/or the alkyl portion is optionally substituted by halogen, oxo, hydroxy, cyano, or combinations thereof (e.g., pyridylethyl, pydridylpropyl, methylpiperazinylethyl, etc.);

R$^8$ is H, or
  alkyl having 1 to 4 carbon atoms, which is branched or unbranched and which is unsubstituted or substituted one or more times by halogen, cyano, and/or C$_{1-4}$-alkoxy (e.g., CH$_3$, C$_2$H$_5$, CHF$_2$, CF$_3$, etc.), and one or more —CH$_2$CH$_2$— groups can be replaced in each case by —CH=CH— or —C≡C—;

$R^9$ is alkoxy or alkylthio, in each case having 1 to 4 carbon atoms, which is branched or unbranched and which is unsubstituted or substituted one or more times by halogen (e.g., $OCH_3$, $OCHF_2$, $OCF_3$, etc.);

$R^{10}$ is —CO—$C_{1-4}$-alkyl which is branched or unbranched and which is unsubstituted or substituted one or more times by halogen (e.g., $CH_3$, $CHF_2$, $CF_3$, etc.), or is

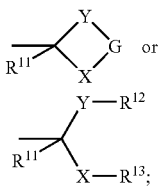

$R^{11}$ is H or alkyl having 1 to 4 carbon atoms, which is branched or unbranched, and which is unsubstituted or substituted one or more times by halogen (e.g., $CH_3$, $CHF_2$, $CF_3$, etc.);

$R^{12}$ is alkyl having 1 to 6 carbon atoms, which is branched or unbranched, and which is unsubstituted or substituted one or more times by halogen (e.g., $CH_3$, $CHF_2$, $CF_3$, etc.);

$R^{13}$ is alkyl having 1 to 6 carbon atoms, which is branched or unbranched, and which is unsubstituted or substituted one or more times by halogen (e.g., $CH_3$, $CHF_2$, $CF_3$, etc.);

X and Y are each independently O or S; and

G is alkylene having 2 to 7 carbon atoms which is unsubstituted or substituted one or more times by halogen; and pharmaceutically acceptable salts thereof;

wherein optically active compounds can be in the form of one of their separate enantiomers or in the form of mixtures thereof, including racemic mixtures.

Corresponding compounds in which the N atom of the pyridyl ring is not in nitroxide form are disclosed in related applications Ser. No. 10/051,309, filed Jan. 22, 2002, Ser. No. 60/396,726, filed Jul. 19, 2002, and Ser. No. 10/622,117, filed Jul. 18, 2003, the entire disclosures of which are incorporated herein by reference.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes but is not limited to inflammatory diseases. These compounds may also function as antidepressants, or be useful in treating cognitive and negative symptoms of schizophrenia.

Assays for determining PDE inhibiting activity as well as selectivity of PDE 4 inhibiting activity and selectivity of inhibiting PDE 4 isoenzymes are known within the art. See, e.g., U.S. Pat. No. 6,136,821, the disclosure of which is incorporated herein by reference.

According to a further aspect of the invention there are provided compounds useful as intermediates for the production of the PDE4 inhibitors described herein (e.g., PDE4 inhibitors of Formulas I–III) and/or useful for the synthesis of radio-labeled analogs of the PDE4 inhibitors with in this application.

Thus, there are provided intermediate compounds which correspond to compounds of Formula I, wherein $R^2$ and $R^3$ are as previously defined for Formula I, but $R^1$ is H, tert-butyldimethylsilyl-, or a suitable phenolic protecting group. Suitable phenolic protecting groups are described, for example, in Greene, T. W. and Wuts, P. G. M., Protective Groups inorganic Synthesis, $3^{rd}$ Edition, John Wiley & Sons, 1999, pp. 246–293. These intermediates are also useful for the synthesis of radio-labeled compounds, such as where $R^1$ is $^3H_3C$—, $^{14}CH_3$— or $^{11}CH_3$—, for example by removing the protecting group and reacting the resultant compound in which $R^1$ is H with suitable radio-labelled reagents. Such radio-labeled compounds are useful for determining compound tissue distribution in animals, in PET imaging studies, and for in vivo, ex vivo, and in vitro binding studies.

Also provided are intermediate compounds which correspond to compounds of Formula I, wherein $R^1$ and $R^3$ are as previously defined for Formula I, but $R^2$ is H, tert-butyldimethylsilyloxy-, or a suitable phenolic protecting group. Suitable phenolic protecting groups are described, for example, in Greene, T. W. and Wuts, P. G. M., Protective Groups in Organic Synthesis, $3^{rd}$ Edition, John Wiley & Sons, 1999, pp. 246–293. Compounds in which $R^2$ is H are useful as intermediates, for example, as scaffolds for parallel or combinatorial chemistry applications. Further, these compounds are useful for the introduction of radio-labels such as $^3H$, $^{14}C$, or $^{11}C$.

Other preferred intermediates are compounds that are in accordance with any one of Formulas I–III, except that $R^3$ is H. Additional radio-labeled compounds that are useful for determining compound tissue distribution in animals, in PET imaging studies, and for in vivo, ex vivo, and in vitro binding studies are compounds according to Formulas I–III wherein $R^3$ is aryl and the aryl structure contains a $^{14}C$ atom in the ring, as well as compounds of Formula III in which $R^9$ is $OCH_3$ in which the C atom is $^{14}C$ or at least one of the H atoms is $^3H$.

Halogen herein refers to F, Cl, Br, and I. Preferred halogens are F and Cl.

Alkyl, as a group or substituent per se or as part of a group or substituent (e.g., alkylamino, trialkylsilyloxy, aminoalkyl, hydroxyalkyl), means generally a straight-chain or branched-chain aliphatic hydrocarbon radical having, for example, 1 to 12 carbon atoms, preferably 1 to 8 carbon atoms, especially 1 to 4 carbon atoms. Suitable alkyl groups include methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, for example, halogens, oxo, hydroxyl, $C_{1-4}$-alkoxy and/or cyano. Halogens are preferred substituents, especially F and Cl.

Alkoxy means alkyl-O— groups and alkoxyalkoxy means alkyl-O-alkyl-O— groups in which the alkyl portions are in accordance with the previous discussion. Suitable alkoxy and alkoxyalkoxy groups include methoxy, ethoxy, propoxy, butoxy, pentoxy, hexoxy, heptoxy, octoxy methoxymethoxy ethoxymethoxy, propoxymethoxy, and methoxyethoxy. Preferred alkoxy groups are methoxy and ethoxy. Similarly, alkoxycarbonyl means alkyl —O—CO— in which the alkyl portion is in accordance with the previous discussion. Examples include methoxycarbonyl, ethoxycarbonyl, propoxycarbonyl, and tert-butoxycarbonyl.

Cycloalkyl means a monocyclic, bicyclic or tricyclic nonaromatic saturated hydrocarbon radical having 3 to 10 carbon atoms, preferably 3 to 8 carbon atoms, especially 3 to 6 carbon atoms. Suitable cycloalkyl groups include cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalklyl groups are cyclopropyl, cyclopentyl and cyclohexyl. The cycloalkyl group can be substituted, for example, substituted by halogens and/or alkyl groups.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, and phenoxy.

Arylalkyl refers to an aryl-alkyl-radical in which the aryl and alkyl portions are in accordance with the previous descriptions. Suitable examples include benzyl, 1-phenethyl, 2-phenethyl, phenpropyl, phenbutyl, phenpentyl, and napthylmethyl.

Heteroaryl refers to an aromatic heterocyclic group having one or two rings and a total number of 5 to 10 ring atoms wherein at least one of the ring atoms is a heteroatom. Preferably, the heteroaryl group contains 1 to 3, especially 1 or 2, hetero-ring atoms which are selected from N, O and S. Suitable heteroaryl groups include furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, e.g., 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7-, 8-isoquinolinyl.

Substituted heteroaryl refers to the heteroaryl groups described above which are substitued in one or more places by, for example, halogen, aryl, alkyl, alkoxy, carboxy, methylene, cyano, trifluoromethyl, nitro, oxo, amino, alkylamino, and dialkylamino.

Heterocycles include heteroaryl groups as described above as well as non-aromatic cyclic groups containing at least one hetero-ring atom, preferably selected from N, S and O, for example, tetrahydrofuranyl, piperidinyl, and pyrrolidinyl.

Heterocycle-alkyl refers to a heterocycle-alkyl-group wherein the heterocyclic and alkyl portions are in accordance with the previous discussions. Suitable examples are pyridylmethyl, thienylmethyl, pyrimidinylmethyl, pyrazinylmethyl, and isoquinolinylmethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C═C bond. Suitable examples are cyclopentenyl, cyclohexenyl, cyclohexadienyl, tetrahydronaphthenyl and indan-2-yl.

Alkenyl refers to straight-chain or branched-chain aliphatic radicals containing 2 to 12 carbon atoms in which one or more —$CH_2$—$CH_2$— structures are each replaced by —CH═CH—. Suitable alkenyl groups are ethenyl, 1-propenyl, 2-methylethenyl, 1-butene, 2-butene, 1-pentenyl, and 2-pentenyl.

Alkynyl refers to straight-chain or branched-chain aliphatic radicals containing 2 to 12 carbon atoms in which one or more —$CH_2$—$CH_2$— structures are each replaced by —C≡C—. Suitable alkynyl groups are ethynyl, propynyl, 1-butynyl, and 2-butynyl.

Acyl refers to alkanoyl radicals having 1 to 13 carbon atoms in which the alkyl portion can be substituted by halogen, alkyl, aryl and/or alkoxy, or aroyl radicals having 7 to 15 carbon atoms in which the aryl portion can be substituted by, for example, halogen, alkyl and/or alkoxy. Suitable acyl groups include formyl, acetyl, propionyl, butanoyl and benzoyl.

Substituted radicals preferably have 1 to 3 substituents, especially 1 to 2 substituents.

In the compounds of Formula I, $R^1$ is an alkyl group having preferably 1 to 4 carbon atoms which is optionally substituted by halogen, preferably fluorine or chlorine. In particular, $R^1$ is preferably methyl or difluoromethyl.

$R^2$ is preferably cycloalkyl, particularly cyclopentyl.

$R^2$ is also preferably aryl or arylalkyl, particularly substituted or unsubstituted phenyl or phenylalkyl, such as phenyl, methylphenyl, methoxyphenyl, chlorophenyl, phenethyl, phenpropyl, phenbutyl, phenylethenyl, phenoxyethyl, phenoxypropyl, phenoxybutyl, chlorophenylethyl, methoxyphenylethyl, chlorophenylethenyl, chlorophenoxyethyl, chlorophenypropyl, methoxyphenpropyl, methoxyphenbutyl, chlorophenbutyl, nitrophenbutyl, chlorophenylaminoethyl, and the like.

$R^2$ is also preferably a partially unsaturated carbocyclic groups, which is unsubstituted or substituted, particularly cyclohexenyl, cyclohexadienyl, indan-2-yl.

$R^2$ is also preferably an alkyl group having 1 to 8 carbon atoms, especially 1 to 4 carbon atoms, which is substituted or unsubstituted, e.g., methyl, difluoromethyl, trifluoromethyl, and methoxyethyl.

$R^2$ is also preferably a heterocyclic or heterocycle-alkyl group, particularly radicals in which the heterocyclic group has 5 to 6 ring atoms and 1 to 2 hetero-ring atoms selected from N, O and S, e.g., tetrahydrofuranyl, pyrrolidinyl, pyrrolyl, pyridylmethyl, pyridylethyl, pyridylpropyl, piperazinylmethyl, piperazinylethyl, methylpiperazinylethyl and the like.

Preferred $R^2$ include cyclopentyl, tetrahydrofuranyl, $CHF_2$, methoxyethyl, cyclopropylmethyl, phenethyl, phenpropyl, phenylethenyl, phenoxyethyl, phenoxybutyl, phenylaminoethyl, indan-2-yl, pyridylethyl, and pyridylpropyl.

In the compounds of Formulas I–III, $R^3$ is preferably aryl or heteroaryl, especially phenyl, naphthyl, biphenyl, furanyl, pyrazinyl, pyrimidinyl, pyridyl, quinolinyl, and isoquinolinyl, which in each case is unsubstituted or is substituted one or more times. Preferred substituents are OH, F, Cl, $CF_3$, alkyl (such as methyl or ethyl), alkoxy (such as methoxy and ethoxy), CN, vinyl, CH$_2$OH, CONHOH, CONH$_2$, methylenedioxy, COOH, and combinations thereof. R$^3$ is preferably pyridyl or phenyl which in each case is substituted or unsubstituted. For example, R$^3$ can be phenyl substituted by halogen, COOH and/or CN.

In addition, when R$^3$ is aryl, especially, phenyl, preferred substituents include R$^4$-L-, e.g., R$^4$—, R$^4$—O—, R$^4$—CO—, R$^4$—NH—CO—, R$^4$—SO$_2$—NH—, R$^4$—SO$_2$—NHCO—, R$^4$—SO$_2$—NH-alkylene-O—, NH$_2$-alkyl-NH—CO—, R$^4$-alkylene-NH—CO—, and alkyl-CO—NH-alkyl-. Other preferred substituents include methyl, ethyl, Cl, F, CN, OCH$_3$, CF$_3$, amino, nitro, CH$_2$OH and COOH.

When R$^3$ is aryl substituted by R$^4$—SO$_2$—NH—, it is preferably a substituted phenyl group and R$^4$ is preferably methyl, ethyl, propyl or phenyl.

When R$^3$ is aryl substituted by R$^4$—SO$_2$—NH-alkylene-O—, it is preferably a substituted phenyl. In such cases, R$^4$ is preferably methyl, ethyl, propyl or phenyl and alkylene is preferably —CH$_2$—, —CH$_2$CH$_2$— or —CH$_2$CH$_2$CH$_2$—.

When R$^3$ is aryl substituted by R$^4$-L-, it is preferably substituted phenyl. In such cases, preferred R$^4$ groups include phenyl, tetrazolyl, oxazinyl, piperazinyl, methylpiperazinyl, pyridyl, methylpyridyl, pyrrolinyl, methylpyrrolinyl, piperadinyl, or methylpiperadinyl, and L is preferably a single bond, —O—, —CO—, —CH$_2$—, —CH$_2$CH$_2$—, —CH$_2$CH$_2$CH$_2$—, —CH$_2$—O—, —CH$_2$CH$_2$—O—, —CH$_2$CH$_2$CH$_2$—O—, —CH$_2$—NH—CH$_2$CH$_2$—O—, —CO—NH—, —NH—CO—, or —CONHSO$_2$—.

R$^6$ is preferably H or F, especially H.

In the compounds of Formula II, R$^7$ can be an alkyl group having preferably 2 to 4 carbon atoms which is optionally substituted by halogen, preferably fluorine or chlorine.

R$^7$ can also preferably be cycloalkyl, particularly cyclopentyl or cyclohexyl.

R$^8$ is preferably H or alkyl having 1 to 4 carbon atoms, especially —C$_2$H$_5$.

In the compounds of Formula III, R$^9$ is preferably alkoxy having 1 to 4 carbon atoms, which is branched or unbranched and which is unsubstituted or substituted one or more times by halogen, e.g., —OCH$_3$ or —OC$_2$H$_5$.

R$^{10}$ is preferably —CO—C$_{1-4}$-alkyl, e.g., —COCH$_3$.

R$^{11}$ is preferably —CH$_3$.

R$^{12}$ and R$^{13}$ are each independently preferably —CH$_3$ or —CH$_2$CH$_3$.

X and Y are each preferably O or S, especially O.

G is preferably —CH$_2$CH$_2$—.

In addition, preferred PDE4 inhibitors in accordance with the invention are compounds described by subformulas Ia-Ix, IIa-IIf, and IIIa-IIIe which correspond, respectfively, to Formulas I–III but exhibit the following preferred groups:

Ia
R$^1$ is methyl or CHF$_2$;
R$^2$ is alkyl, alkenyl, alkynyl, cycloalkyl, arylalkyl, heterocycle-alkyl, cycloalkylalkyl, aryl, or heterocyclic, in each case substituted or unsubstituted; and
R$^3$ is aryl or heteroaryl, in each case substituted or unsubstituted.

Ib
R$^1$ is methyl or CHF$_2$; and
R$^2$ is cyclopentyl, CHF$_2$, cyclopropylmethyl, pyridylethyl (particularly 2-pyridylethyl), or tetrahydrofuranyl (particularly (3R)-tetrahydrofuranyl).

Ic
R$^1$ is methyl or CHF$_2$; and
R$^2$ is cyclopentyl, CHF$_2$, cyclopropylmethyl, pyridylethyl (particularly 2-pyridylethyl), or tetrahydrofuranyl (particularly (3R)-tetrahydrofuranyl); and
R$^3$ is aryl or heteroaryl, in each case substituted or unsubstituted.

Id
R$^1$ is methyl or CHF$_2$;
R$^2$ is cyclopentyl; and
R$^3$ is substituted or unsubstituted aryl or heteroaryl.

Ie
R$^1$ is methyl;
R$^2$ is cyclopentyl; and
R$^3$ is phenyl which is substituted or unsubstituted.

If
R$^1$ is methyl;
R$^2$ is cyclopentyl; and
R$^3$ is phenyl or phenyl substituted with 1 to 3 substituents.

Ig
R$^1$ is methyl;
R$^2$ is cyclopentyl; and
R$^3$ is phenyl, naphthyl, biphenyl, pyridyl, pyrimidinyl, thiazolyl, pyrazinyl, quinolinyl, or isoquinolinyl, in each case substituted or unsubstituted.

Ih
R$^1$ is methyl or CHF$_2$.

Ii
R$^1$ is methyl or CHF$_2$, and
B is N—O.

Ij
R$^1$ is methyl or CHF$_2$, and
R$^2$ is cyclopentyl, CHF$_2$, cyclopropylmethyl, pyridylethyl (particularly 2-pyridylethyl), or tetrahydrofuranyl (particularly (3R)-tetrahydrofuranyl).

Ik
R$^1$ is methyl or CHF$_2$,
B is N—O, and
R$^2$ is cyclopentyl, CHF$_2$, cyclopropylmethyl, pyridylethyl (particularly 2-pyridylethyl), or tetrahydrofuranyl (particularly (3R)-tetrahydrofuranyl).

Il
R$^1$ is methyl or CHF$_2$, and
R$^3$ is 3-pyridyl or phenyl, which in each case is substituted or unsubstituted.

Im
R$^1$ is methyl or CHF$_2$,
B is N—O, and
R$^3$ is 3-pyridyl or phenyl, which in each case is substituted or unsubstituted.

In
R$^1$ is methyl or CHF$_2$,
R$^2$ is cyclopentyl, CHF$_2$, cyclopropylmethyl, pyridylethyl (particularly 2-pyridylethyl), or tetrahydrofuranyl (particularly (3R)-tetrahydrofuranyl), and
R$^3$ is 3-pyridyl or phenyl, which in each case is substituted or unsubstituted.

Io
R$^1$ is methyl or CHF$_2$,
B is N—O,
R$^2$ is cyclopentyl, CHF$_2$, cyclopropylmethyl, pyridylethyl (particularly 2-pyridylethyl), or tetrahydrofuranyl (particularly (3R)-tetrahydrofuranyl), and
R$^3$ is 3-pyridyl or phenyl, which in each case is substituted or unsubstituted.

Ip
  $R^1$ is methyl or $CHF_2$, and
  $R^3$ is phenyl which is substituted in the 3- or 4-position.
Iq
  $R^1$ is methyl or $CHF_2$,
  B is N—O, and
  $R^3$ is phenyl which is substituted in the 3- or 4-position.
Ir
  $R^1$ is methyl or $CHF_2$,
  $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and
  $R^3$ is phenyl which is substituted in the 3- or 4-position.
Is
  $R^1$ is methyl or $CHF_2$,
  B is N—O,
  $R^2$ is cyclopentyl, $CHF_2$, cyclopropyhnethyl, pyridylethyl (particularly 2-pyridylethyl), or tetrahydrofuranyl (particularly (3R)-tetrahydrofuranyl), and
  $R^3$ is phenyl which is substituted in the 3- or 4-position.
It
  $R^1$ is methyl or $CHF_2$, and
  $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.
Iu
  $R^1$ is methyl or $CHF_2$,
  B is N—O, and
  $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.
Iv
  $R^1$ is methyl or $CHF_2$,
  $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and
  $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.
Iw
  $R^1$ is methyl or $CHF_2$,
  B is N—O,
  $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and
  $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 3-nitro-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.
Ix Any of subformulas Ia–Iw wherein $R^6$ is H.
IIa
  $R^3$ is H or is aryl or heteroaryl, in each case substituted or unsubstituted.
IIb
  $R^7$ is cycloalkyl; and
  $R^8$ is H or $C_2H_5$.
IIc
  $R^7$ is cycloalkyl;
  $R^8$ is H or $C_2H_5$; and
  $R^3$ is H or is aryl or heteroaryl, in each case substituted or unsubstituted.
IId
  $R^7$ is cyclopentyl;
  $R^8$ is H or $C_2H_5$; and
  $R^3$ is H or is aryl or heteroaryl, in each case substituted or unsubstituted.
IIe
  $R^7$ is cyclopentyl;
  $R^8$ is H or $C_2H_5$; and
  $R^3$ is phenyl which is substituted or unsubstituted.
IIf Any of subformulas Ia–IIe wherein $R^6$ is H.
IIIa
  $R^3$ is H or is aryl or heteroaryl, in each case substituted or unsubstituted.
IIIb
  $R^9$ is alkoxy having 1 to 4 carbon atoms;
  $R^{10}$ is $COCH_3$ or $R^{11}$ is —$CH_3$;
  X and Y are both O or S; and
  G is —$CH_2CH_2$—.
IIIc
  $R^3$ is H or is aryl or heteroaryl, in each case substituted or unsubstituted;
  $R^9$ is alkoxy having 1 to 4 carbon atoms;
  $R^{10}$ is $COCH_3$ or $R^{11}$ is —$CH_3$;
  X and Y are both O or S; and
  G is —$CH_2CH_2$—.
IIId
  $R^3$ is phenyl which is substituted or unsubstituted;
  $R^9$ is alkoxy having 1 to 4 carbon atoms;
  $R^{10}$ is $COCH_3$ or $R^{11}$ is —$CH_3$;
  X and Y are both O or S; and
  G is —$CH_2CH_2$—.
IIIe Any of subformulas IIIa–IIId wherein $R^6$ is H.

According to a further aspect of the invention, the compounds of formulas I–III are selected from the following:
a) 3'-Chloro-3-cyclopentyloxy-4-methoxy-N-(1-oxy-3-pyridylmethyl)diphenylamine (Which can also be called 3-Chloro-N-(3-cyclopentyloxy-4-methoxyphenyl)-N-(1-oxy-3-pyridylmethyl)aniline)

b) 3'-Chloro-4-methoxy-N-(1-oxy-3-pyridylmethyl)-3-(3-tetrahydrofuryloxy)diphenylamine (Which can also be called 3-Chloro-N-(4-methoxy-3-tetrahydrofuryloxyphenyl)-N-(1-oxy-3-pyridylmethyl)aniline)
c) 3'-Cyano-4-methoxy-N-(1-oxy-3-pyridylmethyl)-3-((3R)-tetrahydrofuryloxy)diphenylamine (Which can also be called 3-Cyano-N-[4-methoxy-3-((3R)-3-tetrahydrofuranyl)oxyphenyl]-N-(1-oxy-3-pyridylmethyl)aniline)
d) 4-Difluoromethoxy-N-(1-oxy-3-pyridylmethyl)-3-(3-tetrahydrofuryloxy)diphenylamine (Which can also be called N-(4-Difluoromethoxy-3-tetrahydrofuryloxyphenyl)-N-(1-oxy-3-pyridylmethyl)aniline)
e) 3,4-Bis(difluoromethoxy)-N-(1-oxy-3-pyridylmethyl)diphenylamine (Which can also be called N-[3,4-Bis(difluoromethoxy)phenyl]-N-(1-oxy-3-pyridylmethyl)aniline)
f) 4-Difluoromethoxy-N-(1-oxy-3-pyridylmethyl)-3-((3R)-tetrahydrofuryloxy)diphenylamine (Which can also be called N-[4-Difluoromethoxy-3-((3R)-3-tetrahydrofuranyl)oxyphenyl]-N-(1-oxy-3-pyridylmethyl)aniline
g) 3'-Cyano-4-difluoromethoxy-N-(1-oxy-3-pyridylmethyl)-3-((3R)-tetrahydrofuryloxy)diphenylamine (Which can also be called 3-Cyano-N-[4-difluoromethoxy-3-((3R)-3-tetrahydrofuranyl)oxyphenyl]-N-(1-oxy-3-pyridylmethyl)aniline)
h) 3'-Chloro-4-difluoromethoxy-N-(1-oxy-3-pyridylmethyl)-3-((3R)-tetrahydrofuryloxy)diphenylamine (Which can also be called 3-Chloro-N-[4-difluoromethoxy-3-((3R)-3-tetrahydrofuranyl)oxyphenyl]-N-(1-oxy-3-pyridylmethyl)aniline)
i) 4'-tert-Butyldimethylsilyloxy-3-cyclopentyloxy-4-methoxy-N-(1-oxy-3-pyridylmethyl)diphenylamine (Which can also be called 4-tert-Butyldimethylsilyloxy-N-(3-cyclopentyloxy-4-methoxyphenyl)-N-(1-oxy-3-pyridylmethyl)aniline)
j) N-(3-Cyclopentyloxy-4-methoxyphenyl)-N-(1-oxy-3-pyridylmethyl)-3-aminobenzoic acid (Which can also be called 3-Amino-N-(3-cyclopentyloxy-4-methoxyphenyl)-N-(1-oxy-3-pyridylmethyl)benzoic acid)
k) N-(3-Cyclopentyloxy-4-methoxyphenyl)-N-(1-oxy-3-pyridylmethyl)-4-aminobenzoic acid (Which can also be called 4-Amino-N-(3-cyclopentyloxy-4-methoxyphenyl)-N-(1-oxy-3-pyridylmethyl)benzoic acid)
l) N-(3-Cyclopentyloxy-4-difluoromethoxyphenyl)-N-(1-oxy-3-pyridylmethyl)-3-aminobenzoic acid (Which can also be called 3-Amino-N-(3-cyclopentyloxy-4-difluoromethoxyphenyl)-N-(1-oxy-3-pyridylmethyl)benzoic acid)
m) N-[4-Methoxy-3-(3-tetrahydrofuryloxy)phenyl]-N-(1-oxy-3-pyridylmethyl)-3-aminobenzoic acid (Which can also be called 3-Amino-N-[4-methoxy-3-(3-tetrahydrofuryloxy)phenyl]-N-(1-oxy-3-pyridylmethyl)benzoic acid)
n) N-3,4-Bis(difluoromethoxy)phenyl)-N-(1-oxy-3-pyridylmethyl)-3-aminobenzoic acid (Which can also be called 3-Amino-N-[3,4-bis(difluoromethoxy)phenyl]-N-(1-oxy-3-pyridylmethyl)benzoic acid)
o) N-[4-methoxy-3-((3R)-tetrahydrofuryloxy)phenyl]-N-(1-oxy-3-pyridylmethyl)-3-aminobenzoic acid (Which can also be called 3-Amino-N-[4-methoxy-3-((3R)-3-tetrahydrofuranyl)oxyphenyl]-N-(1-oxy-3-pyridylmethyl)benzoic acid)
p) N-(3-Cyclopropylmethoxy-4-methoxyphenyl)-N-(1-oxy-3-pyridylmethyl)-4-aminobenzoic acid (Which can also be called 4-Amino-N-(3-cyclopropylmethoxy-4-methoxyphenyl)-N-(1-oxy-3-pyridylmethyl)benzoic acid)
q) N-(3-Cyclopropylmethoxy-4-difluoromethoxyphenyl)-N-(1-oxy-3-pyridylmethyl)-3-aminobenzoic acid (Which can also be called 3-Amino-N-(3-cyclopropylmethoxy-4-difluoromethoxyphenyl)-N-(1-oxy-3-pyridylmethyl)benzoic acid)
r) N-[3-(4-Chlorophenyl)prop-1-yloxy-4-methoxyphenyl]-N-(1-oxy-3-pyridylmethyl)-3-aminobenzoic acid (Which can also be called 3-Amino-N-[3-(4-chlorophenyl)prop-1-yloxy-4-methoxyphenyl]-N-(1-oxy-3-pyridylmethyl)benzoic acid)
s) N-(3-Cyclopropylmethoxy-4-methoxyphenyl)-N-(1-oxy-3-pyridylmethyl)-3-aminobenzoic acid (Which can also be called 3-Amino-N-(3-cyclopropylmethoxy-4-methoxyphenyl)-N-(1-oxy-3-pyridylmethyl)benzoic acid)
t) N-[3-(2-Indanyloxy)-4-methoxyphenyl]-N-(1-oxy-3-pyridylmethyl)-3-aminobenzoic acid (Which can also be called 3-Amino-N-[3-(2-indanyloxy)-4-methoxyphenyl]-N-(1-oxy-3-pyridylmethyl)benzoic acid)
u) N-[4-Methoxy-3-(3-tetrahydrofuryloxy)phenyl]-N-(1-oxy-3-pyridylmethyl)-3-aminobenzoic acid (Which can also be called 3-Amino-N-[4-methoxy-3-(3-tetrahydrofuryloxy)phenyl]-N-(1-oxy-3-pyridylmethyl)benzoic acid)
v) N-[4-Methoxy-3-((3R)-tetrahydrofuryloxy)phenyl]-N-(1-oxy-3-pyridylmethyl)-3-aminobenzoic acid (Which can also be called 3-Amino-N-[4-methoxy-3-((3R)-3-tetrahydrofuranyl)oxyphenyl]-N-(1-oxy-3-pyridylmethyl)benzoic acid)
w) N-[3-(2-Methoxyethoxy)-4-methoxyphenyl]-N-(1-oxy-3-pyridylmethyl)-3-aminobenzoic acid (Which can also be called 3-Amino-N-[3-(2-methoxyethoxy)-4-methoxyphenyl]-N-(1-oxy-3-pyridylmethyl)benzoic acid)
x) 3-Cyclopropylmethyloxy-4-difluoromethoxy-N-(1-oxy-3-pyridylmethyl)-4'-(2H-tetrazol-5-yl)diphenylamine (which can also be called N-(3-Cyclopropylmethyloxy-4-difluoromethoxyphenyl)-N-(1-oxy-3-pyridylmethyl)-4-(2H-tetrazol-5-yl)aniline)
y) 3-Cyclopentyloxy-4-methoxy-N-(1-oxy-3-pyridylmethyl)-4'-(2H-tetrazol-5-yl)diphenylamine (Which can also be called N-(3-Cyclopentyloxy-4-methoxyphenyl)-N-(1-oxy-3-pyridylmethyl)-4-(2H-tetrazol-5-yl)aniline)
z) 3-Cyclopentyloxy-4-methoxy-N-(1-oxy-3-pyridyimethyl)-3'-(2H-tetrazol-5-yl)diphenylamine (Which can also be called N-(3-Cyclopentyloxy-4-methoxyphenyl)-N-(1-oxy-3-pyridylmethyl)-3-(2H-tetrazol-5-yl)aniline)
aa) 4-Methoxy-N-(1-oxy-3-pyridylmethyl)-3-((3R)-tetrahydrofuryloxy)-4'-(2H-tetrazol-5-yl)diphenylamine (Which can also be called N-[4-Methoxy-3-((3R)-3-tetrahydrofuranyl)oxyphenyl]-N-(1-oxy-3-pyridylmethyl)-4-(2H-tetrazol-5-yl)aniline)
bb) 3-Cyclopropylmethyloxy-4-methoxy-N-(1-oxy-3-pyridylmethyl)-4'-(2H-tetrazol-5-yl)diphenylamine (Which can also be called N-(3-Cyclopropylmethyloxy-4-methoxyphenyl)-N-(1-oxy-3-pyridylmethyl)-4-(2H-tetrazol-5-yl)aniline)
cc) 4-Difluoromethoxy-N-(1-oxy-3-pyridylmethyl)-3-((3R)-tetrahydrofuryloxy)-4'-(2H-tetrazol-5-yl)diphenylamine (Which can also be called N-[4-Difluoromethoxy-3-((3R)-3-tetrahydrofuranyl)oxyphenyl]-N-(1-oxy-3-pyridylmethyl)-4-(2H-tetrazol-5-yl)aniline)
dd) 3-Cyclopentyloxy-4-difluromethoxy-N-(1-oxy-3-pyridylmethyl)-4'-(2H-tetrazol-5-yl)diphenylamine (Which can also be called N-(3-Cyclopentyloxy-4-difluromethoxyphenly)-N-(1-oxy-3-pyridylmethyl)-4-(2H-tetrazol-5-yl)aniline)
ee) 3-Cyclopropylmethyloxy-4-difluoromethoxy-N-(1-oxy-3-pyridylmethyl)-3'-(2H-tetrazol-5-yl)diphenylamine (Which can also be called N-(3-Cyclopropylmethyloxy-4-difluoromethoxyphenyl)-N-(1-oxy-3-pyridylmethyl)-3-(2H-tetrazol-5-yl)aniline)

ff) Bis-3,4-difluoromethoxy-N-(1-oxy-3-pyridylmethyl)-4'-(2H-tetrazol-5-yl)diphenylamine (Which can also be called N-[3,4-Bis(difluoromethoxy)phenyl]-N-(1-oxy-3-pyridylmethyl)-4-(2H-tetrazol-5-yl)aniline)

gg) N-(3-Cyclopentyloxy-4-methoxyphenyl)-N-(3-pyridyl)-N-(1-oxy-3-pyridylmethyl)amine (Which can also be called 3-Amino-N-(3-cyclopentyloxy-4-methoxyphenyl)-N-(1-oxy-3-pyridylmethyl)pyridine)

hh) N-(3-Cyclopentyloxy-4-difluoromethoxyphenyl)-N-(3-pyridyl)-N-(1-oxy-3-pyridylmethyl)amine (Which can also be called 3-Amino-N-(3-cyclopentyloxy-4-difluoromethoxyphenyl)-N-(1-oxy-3-pyridylmethyl)pyridine)

ii) N-(3-Cyclopropylmethoxy-4-difluoromethoxyphenyl)-N-(3-pyridyl)-N-(1-oxy-3-pyridylmethyl)amine (Which can also be called 3-Amino-N-(3-cyclopropylmethoxy-4-difluoromethoxyphenyl)-N-(1-oxy-3-pyridylmethyl)pyridine)

jj) N-(4-Difluoromethoxy-3-(3R)-tetrahydrofuryloxyphenyl)-N-(3-pyridyl)-N-(1-oxy-3-pyridylmethyl)amine (Which can also be called 3-Amino-N-[4-difluoromethoxy-3-((3R)-3-tetrahydrofuranyl)oxyphenyl]-N-(1-oxy-3-pyridylmethyl)pyridine)

kk) 3-Cyclopentyloxy-3'-ethanesulfonylamino-4-methoxy-N-(1-oxy-3-pyridylmethyl)diphenylamine (Which can also be called N-(3-Cyclopentyloxy-4-methoxyphenyl)-3-ethylsulfonylamino-N-(1-oxy-3-pyridylmethyl)aniline)

ll) 3-Cyclopentyloxy-4-methoxy-3'-(1-propanesulfonylamino)-N-(1-oxy-3-pyridylmethyl)diphenylamine (Which can also be called N-(3-Cyclopentyloxy-4-methoxyphenyl)-N-(1-oxy-3-pyridylmethyl)-3-(1-propylsulfonylamino)aniline)

mm) 3-Cyclopentyloxy-4'-ethanesulfonylamino-4-methoxy-N-(1-oxy-3-pyridylmethyl)diphenylamine (Which can also be called N-(3-Cyclopentyloxy-4-methoxyphenyl)-4-ethylsulfonylamino-N-(1-oxy-3-pyridylmethyl)aniline)

nn) 3-Cyclopentyloxy-4-methoxy-4'-(1-propanesulfonylamino)-N-(1-oxy-3-pyridylmethyl)diphenylamine (Which can also be called N-(3-Cyclopentyloxy-4-methoxyphenyl)-N-(1-oxy-3-pyridylmethyl)-4-(1-propanesulfonylamino)aniline)

oo) 3-Cyclopropylmethoxy-3'-ethanesulfonylamino-4-methoxy-N-(1-oxy-3-pyridylmethyl)diphenylamine (Which can also be called N-(3-Cyclopropylmethoxy-4-methoxyphenyl)-3-ethylsulfonylamino-N-(1-oxy-3-pyridylmethyl)aniline)

pp) 4-Difluoromethoxy-3'-ethanesulfonylamino-N-(1-oxy-3-pyridylmethyl)-3-[(3R)-tetrahydrofuryloxy]diphenylamine (Which can also be called N-[4-Difluoromethoxy-3-((3R)-3-tetrahydrofuranyl)oxyphenyl]-3-ethylsulfonylamino-N-(1-oxy-3-pyridylmethyl)aniline)

qq) 4-Methoxy-3-[2-(2-pyridyl)ethoxy]-N-(1-oxy-3-pyridylmethyl)diphenylamine (Which can also be called N-[4-Methoxy-3-(2-(2-pyridyl)ethoxyphenyl)]-N-(1-oxy-3-pyridylmethyl)aniline)

rr) 4-Methoxy-N-(1-oxy-3-pyridylmethyl)-3-[(3R)-tetrahydrofuryloxy]diphenylamine (Which can also be called N-[4-Methoxy-3-((3R)-3-tetrahydrofuranyl)oxyphenyl]-N-(1-oxy-3-pyridylmethyl)aniline)

ss) 3'-Chloro-4-methoxy-3-[2-(2-pyridyl)ethoxy]-N-(1-oxy-3-pyridylmethyl)diphenylamine (Which can also be called 3-Chloro-N-[4-methoxy-3-(2-(2-pyridyl)ethoxy)]-N-(1-oxy-3-pyridylmethyl)aniline)

tt) 3'-Chloro-4-methoxy-N-(1-oxy-3-pyridylmethyl)-3-[(3R)-tetrahydrofuryloxy]diphenylamine (Which can also be called 3-Chloro-N-[4-methoxy-3-((3R)-3-tetrahydrofuranyl)oxyphenyl]-N-(1-oxy-3-pyridylmethyl)aniline)

uu) 3-Cyclopentyloxy-4-methoxy-4'-[2-(5-oxopyrrolidinyl)methoxy]-N-(1-oxy-3-pyridylmethyl)diphenylamine (Which can also be called N-(3-Cyclopentyloxy-4-methoxyphenyl)-4-[2-(5-oxopyrrolidinyl)methoxy]-N-(1-oxy-3-pyridylmethyl)aniline)

vv) 3-Cyclopentyloxy-4-methoxy-N-(3-aminocarbonylphenyl)-N-(1-oxy-3-pyridylmethyl)aniline (Which can also be called 3-Aminocarbonyl-N-(3-cyclopentyloxy-4-methoxyphenyl)-N-(1-oxy-3-pyridylmethyl)aniline)

ww) 3,4-Bisdifluoromethoxy-N-(3-carboxy-4-chlorophenyl)-N-(1-oxy-3-pyridylmethyl)aniline (Which can also be called 3-Amino-N-[3,4-Bis(difluoromethoxy)phenyl]-4-chloro-N-(1-oxy-3-pyridylmethyl)benzoic acid)

xx) 3,4-Bisdifluoromethoxy-N-(4-(1-pyrrol-1-yl)phenyl)-N-(1-oxy-3-pyridylmethyl)aniline (Which can also be called N-[3,4-Bis(difluoromethoxy)phenyl]-N-(1-oxy-3-pyridylmethyl)-4-(1-pyrrolyl)aniline yy) 4-Methoxy-3-(R)-tetrahydrofuryloxy-N-(3-carboxy-4-chlorophenyl)-N-(1-oxy-3-pyridylmethyl)aniline (Which can also be called 3-Amino-4-chloro-N-[4-methoxy-3-((3R)-3-tetrahydrofuranyl)oxyphenyl]-N-(1-oxy-3pyridylmethyl)benzoic acid)

zz) 4-Methoxy-3-(R)-tetrahydrofuryloxy-N-(3-carboxyphenyl)-N-(1-oxy-4-pyridylmethyl)aniline (Which can also be called 3-Amino-N-[4-methoxy-3-((3R)-3-tetrahydrofuranyl)oxyphenyl]-N-(1-oxy-4-pyridylmethyl)benzoic acid aaa) 4-Methoxy-3-(R)-tetrahydrofuryloxy-N-(3-pyridyl)-N-(1-oxy-4-pyridylmethyl)aniline (Which can also be called 3-Amino-N-[4-methoxy-3-((3R)-3-tetrahydrofuranyl)oxyphenyl]-N-(1-oxy-4-pyridylmethyl)pyridine)

bbb) 3-Cyclopentyloxy-4-methoxy-N-(4-carboxy-3-chlorophenyl)-N-(1-oxy-3-pyridylmethyl)aniline (Which can also be called 4-Amino-3-chloro-N-(3-cyclopentyloxy-4-methoxyphenyl)-N-(1-oxy-3-pyridylmethyl)benzoic acid)

ccc) 2-Acetyl-7-methoxy-4-(N-(4-cyanophenyl)-N-(1-oxy-3-pyridylmethyl))aminobenzofuran (Which can also be called 2-Acetyl-4-amino-N-(4-cyanophenyl)-7-methoxy-N-(1-oxy-3-pyridylmethyl)benzofuran)

ddd) 2-Acetyl-7-methoxy-4-(N-phenyl-N-(1-oxy-4-pyridylmethyl))aminobenzofuran (Which can also be called 2-Acetyl-4-amino-7-methoxy-N-(1-oxy-4-pyridylmethyl)-N-phenyl-benzofuran)

eee) 2-Acetyl-7-methoxy-4-(N-(3-carboxyphenyl)-N-(1-oxy-3-pyridylmethyl))aminobenzofuran (Which can also be called 2-Acetyl-4-amino-N-(3-carboxyphenyl)-7-methoxy-N-(1-oxy-3-pyridylmethyl)benzofuran fff) 1-Cyclopentyl-3-ethyl-6-(N-(3-carboxyphenyl)-N-(1-oxy-3-pyridylmethyl))aminoindazole (Which can also be called 6-Amino-1-cyclopentyl-3-ethyl-N-(3-carboxyphenyl)-N-(1-oxy-3-pyridylmethyl)indazole)

ggg) 2-Acetyl-7-methoxy-4-(N-(4-acetylphenyl)-N-(1-oxy-3-pyridylmethyl))aminobenzofuran (Which can also be called 2-Acetyl-N-(4-acetylphenyl)-4-amino-7-methoxy-N-(1-oxy-3-pyridylmethyl)benzofuran)

hhh) N-[4-Methoxy-3-((3R)-3-tetrahydrofuranyl)oxyphenyl]-4-methylsulfonylaminocarbonyl-N-(1-oxy-3-pyridylmethyl)aniline iii) 4-(4-Fluorophenyl)sulfonylaminocarbonyl-N-[4-methoxy-3-((3R)-3-tetrahydrofuranyl)oxyphenyl]-N-(1-oxy-3-pyridylmethyl)aniline jjj) 3-Chloro-N-[4-methoxy-3-((3R)-3-tetrahydrofuranyl)oxyphenyl]-N-(1-oxy-3-pyridylmethyl)aniline kkk) 3-Amino-N-(5-fluoro-1-oxy-3-pyridylmethyl)-N-(4-methoxy-3-((3R)-3-tetrahydrofuranyl)oxyphenyl]benzoic acid lll) 3-Amino-N-(3-cyclopentyloxy-4-methoxyphenyl)-N-(1-oxy-2-pyridylmethyl)benzoic acid
mmm) 3-Amino-N-[4-methoxy-3-((3R)-3-tetrahydrofuranyl)oxyphenyl]-N-(1-oxy-3-pyridylmethyl)-5-trifluoromethylbenzoic acid
nnn) 4-Ethylsulfonylaminocarbonyl-N-[4-methoxy-3-((3R)-3-tetrahydrofuranyl)oxyphenyl]-N-(1-oxy-3-pyridylmethyl)aniline
ooo) 4-(2-Fluorophenyl)sulfonylaminocarbonyl-N-[4-methoxy-3-((3R)-3-tetrahydrofuranyl)oxyphenyl]-N-(1-oxy-3-pyridylmethyl)aniline
ppp) 4-(3-Chlorophenyl)sulfonylaminocarbonyl-N-[4-methoxy-3-((3R)-3-tetrahydrofuranyl)oxyphenyl]-N-(1-oxy-3-pyridylmethyl)aniline
qqq) 3-Amino-N-[4-methoxy-3-((3R)-3-tetrahydrofuranyl)oxyphenyl]-N-(1-oxy-3-pyridylmethyl)-6-trifluoromethylbenzoic acid
rrr) 4-Amino-N-[4-difluoromethoxy-3-((3R)-3-tetrahydrofuranyl)oxyphenyl]-N-(1-oxy-3-pyridylmethyl)benzoic acid
sss) N-[4-Difluoromethoxy-3-((3R)-3-tetrahydrofuranyl)oxyphenyl]-4-methylsulfonylaminocarbonyl-N-(1-oxy-3-pyridylmethyl)aniline
ttt) N-[4-Methoxy-3-((3R)-3-tetrahydrofuranyl)oxyphenyl]-N-(1-oxy-3-pyridylmethyl)-4-phenylsulfonylaminocarbonylaniline
uuu) 3-Amino-N-(3-cyclopentyloxy-4-methoxyphenyl)-N-(5-fluoro-1-oxy-3-pyridylmethyl)benzoic acid
vvv) 4-Amino-N-(3-cyclopentyloxy-4-methoxyphenyl)-N-(5-fluoro-1-oxy-3-pyridylmethyl)benzoic acid
www) 3-Amino-N-[4-difluoromethoxy-3-((3R)-3-tetrahydrofuranyl)oxyphenyl]-N-(1-oxy-3-pyridylmethyl)benzoic acid
xxx) 3-Amino-N-(3-cyclobutyloxy-4-methoxyphenyl)-N-(1-oxy-3-pyridylmethyl)benzoic acid
yyy) 3-Amino-N-(3-cyclopentyloxy-4-methoxyphenyl)-5-fluoro-N-(1-oxy-3-pyridylmethyl)benzoic acid
zzz) 3-Amino-N-[3,4-bis(difluoromethoxy)phenyl]-5-fluoro-N-(1-oxy-3-pyridylmethyl)benzoic acid
aaaa) 4-Amino-N-(3-cyclobutyloxy-4-methoxyphenyl)-N-(1-oxy-3-pyridylmethyl)benzoic acid
bbbb) 4-Amino-N-(3-ethoxy-4-methoxyphenyl)-N-(1-oxy-3-pyridylmethyl)benzoic acid
cccc) 4-Amino-N-(3-isopropoxy-4-methoxyphenyl)-N-(1-oxy-3-pyridylmethyl)benzoic acid
dddd) N-[4-Difluoromethoxy-3-((3R)-3-tetrahydrofuranyl)oxyphenyl]-4-(3,4-difluorophenyl)sulfonylaminocarbonyl-N-(1-oxy-3-pyridylmethyl)aniline
eeee) 4-Amino-N-(3-cyclopropylmethoxy-4-methoxyphenyl)-N-(1-oxy-3-pyridylmethyl)benzoic acid
ffff) N-[3,4-Bis(difluoromethoxy)phenyl]-4-(4-fluorophenyl)sulfonylaminocarbonyl-N-(1-oxy-3-pyridylmethyl)aniline
gggg) 4-(2,4-Difluorophenyl)sulfonylaminocarbonyl-N-[4-methoxy-3-((3R)-3-tetrahydrofuranyl)oxyphenyl]-N-(1-oxy-3-pyridylmethyl)aniline
hhhh) 4-(3,4-Difluorophenyl)sulfonylaminocarbonyl-N-[4-methoxy-3-((3R)-3-tetrahydrofuranyl)oxyphenyl]-N-(1-oxy-3-pyridylmethyl)aniline
iiii) N-[4-Difluoromethoxy-3-((3R)-3-tetrahydrofuranyl)oxyphenyl]-4-ethylsulfonylaminocarbonyl-N-(1-oxy-3-pyridylmethyl)aniline
jjjj) 3-Amino-N-(3,4-dimethoxyphenyl)-N-(1-oxy-3-pyridylmethyl)benzoic acid
kkkk) 3-Amino-N-(3-ethoxy-4-methoxyphenyl)-N-(1-oxy-3-pyridylmethyl)benzoic acid
llll) 3-Amino-N-(3-isopropoxy-4-methoxyphenyl)-N-(1-oxy-3-pyridylmethyl)benzoic acid
mmmm) 4-(3,4-Difluorophenyl)sulfonylaminocarbonyl-N-(3-ethoxy-4-methoxyphenyl)-N-(1-oxy-3-pyridylmethyl)aniline
nnnn) 3-Amino-N-[3,4-bis(difluoromethoxy)phenyl]-N-(1-oxy-3-pyridylmethyl)benzoic acid
oooo) 3-Amino-N-(4-difluoromethoxy-3-ethoxyphenyl)-N-(1-oxy-3-pyridylmethyl)benzoic acid
pppp) 4-Amino-N-(4-difluoromethoxy-3-ethoxyphenyl)-N-(1-oxy-3-pyridylmethyl)benzoic acid
qqqq) 3-Amino-N-(4-difluoromethoxy-3-methoxyphenyl)-N-(1-oxy-3-pyridylmethyl)benzoic acid
rrrr) 2-Acetyl-7-methoxy-4-(N-phenyl-N-(1-oxy-3-pyridylmethyl))aminobenzofuran,
ssss) 4-Amino-N-(3-cyclopentyloxy-4-methoxyphenyl)-N-(1-oxypyridin-3-ylmethyl)pyridine,
tttt) N-[Bis-3,4-(difluoromethoxy)phenyl]-N-(1-oxy-3-pyridylmethyl)-4-[2-(2-tetrahydropyranyl)-2H-tetrazol-5-yl]aniline,
uuuu) N-[Bis-3,4-(difluoromethoxy)phenyl]-N-(1-oxy-3-pyridylmethyl)-3-(2H-tetrazol-5-yl)aniline; and
pharmaceutically acceptable salts thereof, wherein optically active compounds can be in the form of their separate enantiomers or mixtures thereof, including racemic mixtures.

Preferred aspects include pharmaceutical compositions comprising a compound of this invention and a pharmaceutically acceptable carrier and, optionally, another active agent as discussed below; a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating neurological syndrome, e.g., loss of memory, especially long-term memory, cognitive impairment or decline, memory impairment, etc. a method of treating a disease state modulated by PDE4 activity, in a mammal, e.g., a human, e.g., those mentioned herein.

The compounds of the present invention may be prepared conventionally. Some of the processes which can be used are described below. All starting materials are known or can be conventionally prepared from known starting materials.

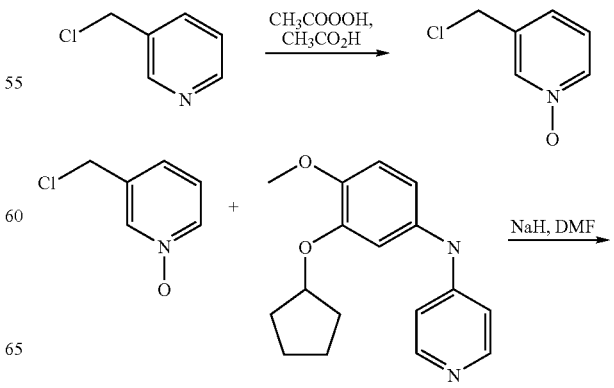

-continued

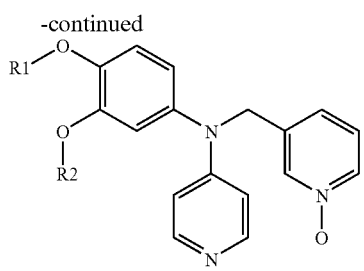

The reaction scheme shown above is for illustrative purposes only and should not be viewed as limiting the scope of the synthetic methods available for the production of the compounds described within this application. Pyridine N-oxides can be produced by methods common within the art, such as by the reaction of the corresponding pyridine with peroxides, e.g., hydrogen peroxide, mCPBA or peracetic acid, in halogenated solvents, such as chloroform or dichloromethane, or in polar protic solvents, such as acetic acid. Thus, for example, the reaction of 3-chloromethylpyridine with peracetic acid in acetic acid/chloroform yields the desired 3-chloromethylpyridine N-oxide as a white crystalline solid.

Subsequently, the anion of the diphenylamine or substituted aniline is prepared by reaction with a strong base, such as sodium hydride, LDA, or potassium hexamethyldisilylazide, in polar aprotic solvents such as DMF or THF. Treatment of the anion of the diphenylamine or substituted aniline with a halomethylpyridine N-oxide provides the desired compounds.

Many of these synthetic procedures are described more fully in the examples below.

One of ordinary skill in the art will recognize that some of the compounds of Formulae I–III can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, and substantially pure and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel O D and Chiracel O J among many others, all routinely selectable. Enzymatic separations, with or without derivitization, are also useful. The optically active compounds of Formulae I–III can likewise be obtained by chiral syntheses utilizing optically active starting materials.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds VIA organometallic intermediates. Tetrahedron (1989), 45(21), 6601–21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1–2), 9–32. CODEN: JRACBN ISSN:0022-4081, CAN 95:76229 AN 1981:476229 CAPLUS.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulas I-III containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553–1593 (current edition).

In view of their high degree of PDE4 inhibition, the compounds of the present invention can be administered to anyone requiring or desiring PDE4 inhibition, and/or enhancement of cognition. Administration may be accomplished according to patient needs, for example, orally, nasally, parenterally (subcutaneously, intraveneously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below its usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The present invention includes methods for dealing with memory loss separate from dementia, including mild cognitive impairment (MCI) and age-related cognitive decline. The present invention includes methods of treatment for memory impairment as a result of disease. In another application, the invention includes methods for dealing with memory loss resulting from the use of general anesthetics, chemotherapy, radiation treatment, post-surgical trauma, and therapeutic intervention.

The compounds may be used to treat psychiatric conditions including schizophrenia, bipolar or manic depression, major depression, and drug addiction and morphine dependence. These compounds may enhance wakefulness. PDE4 inhibitors can be used to raise cAMP levels and prevent neurons from undergoing apoptosis. PDE4 inhibitors are also known to be anti-inflammatory. The combination of anti-apoptotic and anti-inflammatory properties make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Thus, in accordance with a preferred embodiment, the present invention includes methods of treating patients suffering from memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, Rubenstein-Taybi syndrome (RSTS), depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases, comprising administering an effective amount of a compound according to Formulas I-III or pharmaceutically acceptable salts thereof.

The compounds of the present invention can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

The compounds of the present invention can also be used in methods of treating patients suffering from obesity and in treatment methods for neuronal regeneration or neurogenesis.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to Formulae I–III or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

PDE4 inhibitors for treating asthma, chronic bronchitis, psoriasis, allergic rhinitis, and other inflammatory diseases, and for inhibiting tumor necrosis factor are known within the art. See, e.g., WO 98/58901, JP11-189577, JP 10-072415, WO 93/25517, WO 94/14742, U.S. Pat. Nos. 5,814,651, and 5,935,978. These references also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The invention is also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also know as Kennedy disease (androgen receptor).

Thus, in accordance with a further aspect of the invention, there is provided a method of treating a polyglutamine-repeat disease or CAG repeat expansion disease comprising administering to a patient, especially a human, a therapeutically effective amount of a compound according to Formulas I–III. In accordance with a further embodiment, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, especially a human, a therapeutically effective amount of a compound according to Formulas I–III.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, choinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of, for example, 0.01–100 mg/kg/day, preferably 0.1–70 mg/kg/day, especially 0.5–10 mg/kg/day. Unit dosage forms can contain, for example, 0.1–50 mg of active compound. For intravenous administration, the compounds can be administered, in single or multiple dosages, at a dosage level of, for example, 0.001–50 mg/kg/day, preferably 0.001–10 mg/kg/day, especially 0.01–1 mg/kg/day. Unit dosage forms can contain, for example, 0.1–10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLE 1

3-Chloromethylpyridine N-Oxide Picolyl chloride hydrochloride (8.0 g, 49 mmol) is dissolved in ice cold, saturated, aqueous sodium bicarbonate (100 mL) and the mixture is extracted with 2×100 mL chloroform. The chloroform extracts are dried ($MgSO_4$) and filtered. 32% Peracetic acid in acetic acid (50 mL) is added to the filtrate and the mixture is vigorously stirred for 18 h. The mixture is washed twice with cold, sat., aq. $NaHCO_3$, dried ($MgSO_4$), and concentrated in vacuo. The solid obtained is triturated with hexanes and dried in vacuo to give 3-chloromethylpyridine N-oxide (2.0 g, 29% yield) as a white crystalline solid.

1H NMR (300 mHz, $CDCl_3$) δ 8.16 (s, 1H), 8.03 (m, 1H), 7.13–7.23 (m, 2H), 4.04 (s, 2H).

The compounds 2-chloromethylpyridine N-oxide and 4-chloromethylpyridine N-oxide can be prepared in a similar manner.

EXAMPLE 2

4-Amino-N-(3-cyclopentyloxy-4-methoxyphenyl)-N-(1-oxy-3-pyridylmethyl)pyridine

4-Amino-N-(3-cyclopentyloxy-4-methoxyphenyl)pyridine (0.28 g, 1.0 mmol) was dissolved in DMF (1 mL) and added drop-wise to a stirred suspension of NaH (200 mg of a 60% mineral oil dispersion, 5.0 mmol) in DMF (4 mL) at room temperature. After addition was complete, the mixture was stirred for 0.5 h at room temperature and 3-chloromethylpyridine N-oxide (300 mg, 2.0 mmol) was added in one portion. The mixture was stirred for 4 h, then carefully quenched with water and partitioned between EtOAc (50 mL) and water (50 mL). The EtOAc layer was washed with water (25 mL) and brine (25 mL), dried ($MgSO_4$), and concentrated in vacuo. The residue was purified by flash column chromatography (silica gel) eluting with 30% MeOH in EtOAc to give 4-amino-N-(3-cyclopentyloxy-4-methoxyphenyl)-N-(1-oxypyridin-3-ylmethyl)pyridine (64 mg, 16% yield).

1H NMR (300 mHz, $CDCl_3$) δ 8.16 (m, 3H), 8.08 (d, 1H, J=6.0 Hz), 7.20–7.60 (m, 2H), 6.85 (d, 2H, J=8.5), 6.72 (dd, 1H, J=8.4, 2.4), 6.66 (s, J=2.4 Hz, 2H), 6.40–6.50 (m, 2H), 4.82 (s, 2H), 4.65 (m, 1H), 3.82 (s, 3H), 1.60–1.90 (m, 6H), 1.50–1.60 (m, 2H).

The following compounds were prepared in a similar fashion as described above:
a) tert-Butyl 3-Amino-N-(3-cyclopentyloxy-4-methoxyphenyl)-N-(1-oxy-3-pyridylmethyl)benzoate
b) tert-Butyl 4-Amino-N-(3-cyclopentyloxy-4-methoxyphenyl)-N-(1-oxy-3-pyridylmethyl)benzoate
c) N-[Bis-3,4-(difluoromethoxy)phenyl]-N-(1-oxy-3-pyridylmethyl)-4-[2-(2-tetrahydropyranyl)-2H-tetrazol-5-yl]-aniline
d) 3-Chloro-N-[4-methoxy-3-((3R)-3-tetrahydrofuranyl)oxyphenyl]-N-(1-oxy-3-pyridylmethyl)aniline MS (ES): m/z 427 [M+1]
e) tert-Butyl 3-Amino-N-[bis-3,4-(difluoromethoxy)phenyl]-N-(1-oxy-3-pyridylmethyl)benzoate

EXAMPLE 3

4-Amino-N-(3-cyclopentyloxy-4-methoxyphenyl)-N-(1-oxy-3-pyridylmethyl)benzoic acid A solution consisting of 1.75 g (3.44 mmol) of tert-butyl 4-Amino-N-(3-cyclopentyloxy-4-methoxyphenyl)-N-(1-oxy-3-pyridylmethyl)benzoate, 33.5 mL of dichloromethane and 8.4 mL of trifluoroacetic acid was stirred at room temperature for 5 hours. The solution was washed with 50 mL of $H_2O$. Then 50 mL of $H_2O$ was added and the pH adjusted to 6 by the addition of 10% aqueous NaOH. The combined aqueous layers were extracted with 2×50 mL of dichloromethane. The combined dichloromethane extracts were evaporated and the remaining material was purified by flash chromatography over SiO$_2$ using 10% MeOH in CH$_2$Cl$_2$ as eluant. The material was triturated with CH$_3$CN to yield 1.09 g (73% yield) of the title compound as a tan powder. $^1$H NMR (300 MHz, CDCl$_3$) δ 8.57 (s, 1H), 8.23 (d, J=6.3 Hz, 1H), 7.72 (d, J=9.0, 2H), 7.4–7.2 (m, 2H), 6.9–6.7 (m, 3H), 6.58 (d, J=9.0, 2H), 4.94 (s, 2H), 4.71 (m, 1H), 3.83 (s, 3H), 2.0–1.7 (m, 6H), 1.7–1.5 (m, 2H). MS (ES): m/z 435 [M+1]

The following compounds were prepared in a similar manner as described above:

3-Amino-N-(3-cyclopentyloxy-4-methoxyphenyl)-N-(1-oxy-3-pyridylmethyl)benzoic acid MS (ES): m/z 435 [M+1]

3-Amino-N-[bis-3,4-(difluoromethoxy)phenyl]-N-(1-oxy-3-pyridylmethyl)benzoic acid MS (ES): m/z 453.1 [M+1]

EXAMPLE 4

N-[Bis-3,4-(difluoromethoxy)phenyl]-N-(1-oxy-3-pyridylmethyl)-3-(2H-tetrazol-5-yl)aniline N-[Bis-3,4-(difluoromethoxy)phenyl]-N-(1-oxy-3-pyridylmethyl)-4-[2-(2-tetrahydropyranyl)-2H-tetrazol-5-yl]-aniline (1.5 g, 0.26 mmol) was dissolved in THF (5 mL) and 3 mL of 1N HCl was added. After 6 h at room temperature, the mixture was neutralized to pH=5 with saturated aqueous sodium bicarbonate and extracted with EtOAc (3×50 mL). The EtOAc extracts were combined, washed with brine (50 mL), dried (MgSO$_4$), and concentrated in vacuo. The crude residue was loaded onto a RediSep column (10 g, silica gel) and the product was eluted using a linear gradient from 0% MeOH in EtOAc to 5% MeOH in EtOAc over 20 min to give 0.96 g of product as a white powder. $^1$H NMR (300 MHz, CDCl$_3$) δ 8.48 (s, 1H), 8.21 (d, J=6.3 Hz, 1H), 7.77 (m, 2H), 7.50 (d, J=8.0 Hz, 1H), 7.4–7.3 (m, 2H), 7.12 (m, 2H), 6.9–6.8 (m, 2H), 6.51 (t, J=73.6 Hz, 1H), 6.48 (t, J=73.6 Hz, 1H), 5.08 (s, 2H). MS (ES): m/z 477.0 [M+1]

EXAMPLE 5

In Vitro Measurement of Type 4 Phosphodiesterase Inhibition Activity

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 mM MgCl$_2$, 3 uM cAMP, 0.002 U 5'-nucleotidase, and 3×10$^4$ cpm of [3H]cAMP. The reaction was stopped by adding 100 µl of boiling 5 mN HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Wallac Triflux®.

All test compounds are dissolved in 100% DMSO and diluted into the assay such that the final concentration of DMSO is 0.1%. DMSO does not affect enzyme activity at this concentration.

A decrease in adenosine concentration is indicative of inhibition of PDE activity. pIC$_{50}$ values were determined by screening 6 to 12 concentrations of compound ranging from 0.1 nM to 10,000 nM and then plotting drug concentration versus $^3$H-adenosine concentration. Nonlinear regression software (Assay Explorer®) was used to estimate pIC$_{50}$ values.

IC$_{50}$ values for the preferred compounds of the invention are less than 1000 nM, especially less thn 100 nM.

EXAMPLE 6

Method A

Passive Avoidance in Rats, an in vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Sprague-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg MK-801 or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naïve rats required less than 30 seconds, on average, to cross from the illuminated compartment to the darkened compartment. However, 24 hours after the electric shock exposure, most rats pretreated with vehicle did not re-enter the darkened compartment; the average latency was increased up to 175 seconds (p<0.001). Pretreatment with MK-801 (0.1 mg/kg) markedly reduced this latency when compared to the vehicle (p<0.001). This amnesic effect of MK-801 is reversed in a statistically significant manner by actual test compounds in a dose-dependent fashion.

EXAMPLE 6

Method B

Radial Arm Maze Task in Rats, an In vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). Five days after initial housing, rats (male Spraque-Dawley (Harlan) weighing 250 to 350 g) were placed in the eight-arm radial maze (each arm was 60×10× 12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. MK-801 or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests. Compared to control, MKT.-801 (0.1 mg/kg, i.p.) increased the frequencies of both working and reference memory errors (p<0.01). This amnesic effect of MK-801 on working memory is reversed in a statistically significant manner by the administration of actual test compounds in a dose-dependent fashion.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention

We claim:
1. An isolated compound of Formulas I–III:

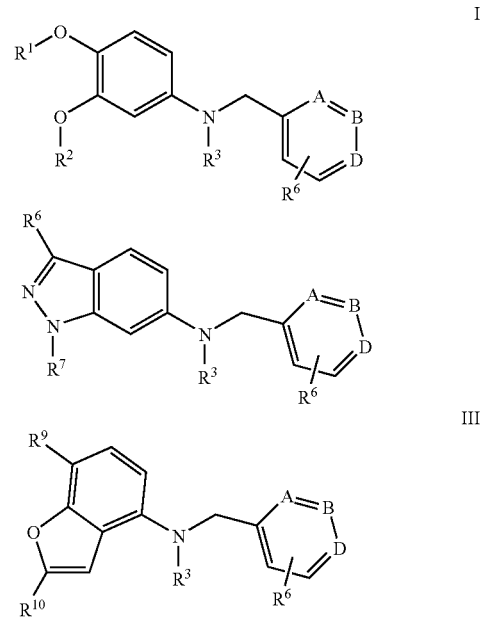

wherein
one of A, B and D is N—O and the others are $CR^6$;
   $R^1$ is alkyl having 1 to 4 carbon atoms, which is branched or unbranched and which is unsubstituted or substituted one or more times by halogen;
   $R^2$ is alkyl having 1 to 12 carbon atoms which is branched or unbranched and which is unsubstituted or substituted one or more times by halogen, hydroxy, cyano, $C_{1-4}$-alkoxy, oxo or combinations thereof, and wherein optionally one or more —CH$_2$CH$_2$— groups is replaced in each case by —CH=CH— or —C≡C—,
   cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof,
   cycloalkylalkyl having 4 to 16 carbon atoms which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof,
   aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, cyano, or combinations thereof,
   arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, $CF_3$, $OCF_3$, alkyl, hydroxy, alkoxy, nitro, cyano, methylenedioxy, ethylenedioxy, or combinations thereof, and wherein in the alkyl portion one or more —CH$_2$CH$_2$— groups are each optionally replaced by —CH=CH— or —C≡C—, and/or one or more —CH$_2$— groups are each optionally replaced by —O— or —NH— and/or the alkyl portion is optionally substituted by halogen, oxo, hydroxy, cyano, or combinations thereof, a partially unsaturated carbocyclic group having 5 to 14 carbon atoms, which is unsubstituted or substituted one or more times by halogen, alkyl, alkoxy, hydroxy, nitro, cyano, oxo, or combinations thereof, a heterocyclic group, which is saturated, partially saturated or unsaturated, having 5 to 10 ring atoms in which at least 1 ring atom is an N, O or S atom, wherein the heterocyclic group is unsubstituted or substituted one or more times by halogen, hydroxy, aryl, alkyl, alkoxy, cyano, trifluoromethyl, nitro, oxo, or combinations thereof, or a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted or substituted one or more times in the heterocyclic portion by halogen, OCF$_3$, hydroxy, aryl, alkyl, alkoxy, cyano, trifluoromethyl, nitro, oxo, or combinations thereof, wherein in the alkyl portion one or more —CH$_2$CH$_2$— groups are each optionally replaced by —CH═CH— or —C≡C—, and/or one or more —CH$_2$— groups are each optionally replaced by —O— or —NH— and/or the alkyl portion is optionally substituted by halogen, oxo, hydroxy, cyano, or combinations thereof;

$R^3$ is H, cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof, aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, OCF$_3$, amino, aminoalkyl, aminoalkoxy dialkylamino, hydroxyalkyl, hydroxamic acid, pyrrolyl, tetrazole-5- yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof, heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof, or a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, trifluoromethyl, nitro, oxo, or combinations thereof;

$R^4$ is H, alkyl having 1 to 8 carbon atoms which is unsubstituted or substituted one or more times by halogen, C$_{1-4}$-alkyl, C$_{1-4}$-alkoxy, oxo, or combinations thereof, alkylamino or dialkylamino wherein each alkyl portion has independently 1 to 8 carbon atoms, a partially unsaturated carbocycle-alkyl group wherein the carbocyclic portion has 5 to 14 carbon atoms and the alkyl portion has 1 to 5 carbon atoms, which is unsubstituted or substituted one or more times by halogen, alkyl, alkoxy, nitro, cyano, oxo, or combinations thereof, cycloalkyl having 3 to 10 carbon atoms which is unsubstituted or substituted one or more times by halogen, hydroxy, oxo, cyano, alkoxy, alkyl having 1 to 4 carbon atoms, or combinations thereof, cycloalkylalkyl having 4 to 16 carbon atoms which is unsubstituted or substituted in the cycloalkyl portion and/or the alkyl portion one or more times by halogen, oxo, cyano, hydroxy, alkyl, alkoxy or combinations thereof, aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy, dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, cycloalkyl, aryl, heteroaryl, or combinations thereof, arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH═CH— or —C≡C—, and/or one or more —CH$_2$— groups are each optionally replaced by —O— or —NH—, a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, CF$_3$O, nitro, oxo, amino, alkylamino, dialkylamino, or combinations thereof and/or substituted in the alkyl portion by halogen, cyano, or methyl or combinations thereof;

L is a single bond or a divalent aliphatic radical having 1 to 8 carbon atoms wherein one or more —CH$_2$— groups are each optionally replaced by —O—, —S—, —SO—, —SO$_2$—, —NR$^5$—, —SO$_2$NH—, —NHSO$_2$—, —SO$_2$NR$^5$—, —NR$^5$SO$_2$—, —CO—, —NR$^5$CO—, —CONR$^5$—, —NHCONH—, —OCONH—, —NHCOO—, —SCONH—, —SCSNH—, or —NHCSNH—;

R$^5$ is H,
  alkyl having 1 to 8 carbon atoms, which is branched or unbranched and which is unsubstituted or substituted one or more times by halogen, C$_{1-4}$-alkyl, C$_{1-4}$-alkoxy, oxo, or combinations thereof,
  aryl having 6 to 14 carbon atoms and which is unsubstituted or substituted one or more times by halogen, alkyl, hydroxy, alkoxy, alkoxyalkoxy, nitro, ethylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, or combinations thereof, or
  arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH=CH— or —C≡C—, and/or one or more —CH$_2$— groups are each optionally replaced by —O— or —NH—;

R$^6$ is H, halogen, alkyl having 1 to 4 carbon atoms, alkoxy having 1 to 4 carbon atoms, CN, or hydroxyl;

R$^7$ is H,
  alkyl having 1 to 8 carbon atoms, which is branched or unbranched and which is unsubstituted or substituted one or more times by halogen, cyano, hydroxy, C$_{1-4}$-alkoxy, or combinations thereof
  cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof,
  cycloalkylalkyl having 4 to 16 carbon atoms which is unsubstituted or substituted in the cycloalkyl portion and/or the alkyl portion one or more times by halogen, oxo, cyano, hydroxy, C$_{1-4}$-alkyl, C$_{1-4}$-alkoxy or combinations thereof,
  aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, cyano, or combinations thereof,
  arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, CF$_3$, OCF$_3$, alkyl, hydroxy, alkoxy, nitro, cyano, methylenedioxy, ethylenedioxy, or combinations thereof, and wherein in the alkyl portion one or more —CH$_2$CH$_2$— groups are each optionally replaced by —CH=CH— or —C≡C—, and/or one or more —CH$_2$— groups are each optionally replaced by —O— or —NH— and/or the alkyl portion is optionally substituted by halogen, oxo, hydroxy, cyano, or combinations thereof,
  a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or
  a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, CF$_3$O, nitro, oxo, amino, alkylamino, dialkylamino, or combinations thereof and/or substituted in the alkyl portion by halogen, cyano, or methyl or combinations thereof;

R$^8$ is H, or
  alkyl having 1 to 4 carbon atoms, which is branched or unbranched and which is unsubstituted or substituted one or more times by halogen, cyano, and/or C$_{1-4}$-alkoxy, and one or more —CH$_2$CH$_2$— groups can be replaced in each case by —CH=CH— or —C≡C—;

R$^9$ is alkoxy or alkylthio, in each case having 1 to 4 carbon atoms, which is branched or unbranched and which is unsubstituted or substituted one or more times by halogen;

R$^{10}$ is —CO—C$_{1-4}$-alkyl which is branched or unbranched and which is unsubstituted or substituted one or more times by halogen, or is

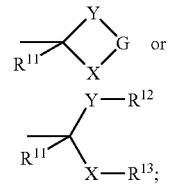

R$^{11}$ is H or alkyl having 1 to 4 carbon atoms, which is branched or unbranched, and which is unsubstituted or substituted one or more times by halogen;

R$^{12}$ is alkyl having 1 to 6 carbon atoms, which is branched or unbranched, and which is unsubstituted or substituted one or more times by halogen;

R$^{13}$ is alkyl having 1 to 6 carbon atoms, which is branched or unbranched, and which is unsubstituted or substituted one or more times by halogen;

X and Y are each independently O or S; and

G is alkylene having 2 to 7 carbon atoms which is unsubstituted or substituted one or more times by halogen; or a pharmaceutically acceptable salt thereof;
wherein an optically active compound can be in the form of one of its separate enantiomers or mixtures thereof, including racemic mixtures.

2. An isolated compound according to claim 1, wherein B is N—O.

3. An isolated compound according to claim 1, wherein said compound is of Formula I and $R^1$ is methyl or difluoromethyl.

4. An isolated compound according to claim 1, wherein said compound is of Formula I and $R^2$ is cycloalkyl.

5. An isolated compound according to claim 1, wherein said compound is of Formula I and $R^2$ is phenyl, methylphenyl, methoxyphenyl, chlorophenyl, phenethyl, phenpropyl, phenbutyl, phenylethenyl, phenoxyethyl, phenoxypropyl, phenoxybutyl, chlorophenylethyl, methoxyphenylethyl, chlorophenylethenyl, chlorophenoxyethyl, chlorophenylpropyl, methoxyphenpropyl, methoxyphenbutyl, chlorophenbutyl, nitrophenbutyl, or chlorophenylaminoethyl.

6. An isolated compound according to claim 1, wherein said compound is of Formula I and $R^2$ is cyclohexenyl, cyclohexadienyl, or indan-2-yl.

7. An isolated compound according to claim 1, wherein said compound is of Formula I and $R^2$ is methyl, difluoromethyl, trifluoromethyl, or methoxyethyl.

8. An isolated compound according to claim 1, wherein said compound is of Formula I and $R^2$ is tetrahydrofuranyl, pyrrolidinyl, pyrrolyl, pyridylmethyl, pyridylethyl, pyridylpropyl, piperazinylmethyl, piperazinylethyl, or methylpiperazinylethyl.

9. An isolated compound according to claim 1, wherein said compound is of Formula I and $R^2$ cyclopentyl, tetrahydrofuranyl, $CHF_2$, methoxyethyl, cyclopropylmethyl, phenethyl, phenpropyl, phenylethenyl, phenoxyethyl, phenoxybutyl, phenylaminoethyl, indan-2-yl, pyridylethyl, or pyridylpropyl.

10. An isolated compound according to claim 1, wherein $R^3$ is phenyl, naphthyl, biphenyl, furanyl, pyrazinyl, pyrimidinyl, pyridyl, quinolinyl, or isoquinolinyl, which in each case is unsubstituted or is substituted one or more times.

11. An isolated compound according to claim 10, wherein $R^3$ is substituted by OH, F, Cl, $CF_3$, methyl, ethyl, methoxy, ethoxy, CN, vinyl, $CH_2OH$, CONHOH, $CONH_2$, methylenedioxy, COOH, or combinations thereof.

12. An isolated compound according to claim 1, wherein $R^3$ is pyridyl or phenyl which in each case is substituted or unsubstituted.

13. An isolated compound according to claim 1, wherein $R^3$ is phenyl substituted by halogen, COOH and/or CN.

14. An isolated compound according to claim 1, wherein $R^3$ is aryl substituted by $R^4$—, $R^4$—O—, $R^4$—CO—, $R^4$—NH—CO—, $R^4$—$SO_2$—NH—, $R^4$—$SO_2$—NHCO—, $R^4$—$SO_2$—NH-alkylene-O—, $NH_2$-alkyl-NH—CO—, $R^4$-alkylene-NH—CO—, alkyl-CO—NH-alkyl-, methyl, ethyl, Cl, F, CN, $OCH_3$, $CF_3$, amino, nitro, $CH_2OH$ or COOH.

15. An isolated compound according to claim 1, wherein $R^3$ is phenyl substituted by $R^4$—$SO_2$—NH— and $R^4$ is methyl, ethyl, propyl or phenyl.

16. An isolated compound according to claim 1, wherein $R^3$ is phenyl substituted by $R^4$—$SO_2$—NH-alkylene-O—, $R^4$ is methyl, ethyl, propyl or phenyl, and alkylene is —$CH_2$—, —$CH_2CH_2$— or —$CH_2CH_2CH_2$—.

17. An isolated compound according to claim 1, wherein $R^3$ is phenyl substituted by $R^4$-L-, $R^4$ is phenyl, tetrazolyl, oxazinyl, piperazinyl, methylpiperazinyl, pyridyl, methylpyridyl, pyrrolinyl, methylpyrrolinyl, piperadinyl, or methylpiperadinyl, and L is a single bond, —O—, —CO—, —$CH_2$—, —$CH_2CH_2$—, —$CH_2CH_2CH_2$—, —$CH_2$—O—, —$CH_2CH_2$—O—, —$CH_2CH_2CH_2$—O—, —$CH_2$—NH—$CH_2CH_2$—O—, —CO—NH—, —NH—CO—, or —$CONHSO_2$—.

18. An isolated compound according to claim 1, wherein $R^6$ is H or F.

19. An isolated compound according to claim 1, wherein $R^6$ is H.

20. An isolated compound according to claim 1, wherein said compound is of Formula II and $R^7$ is alkyl having 2 to 4 carbon atoms which is optionally substituted by halogen.

21. An isolated compound according to claim 1, wherein said compound is of Formula II and $R^7$ is cyclopentyl or cyclohexyl.

22. An isolated compound according to claim 1, wherein said compound is of Formula II and $R^8$ H or $C_2H_5$.

23. An isolated compound according to claim 1, wherein said compound is of Formula III and $R^9$ is $CH_3$ or $C_2H_5$.

24. An isolated compound according to claim 1, wherein said compound is of Formula III and $R^{10}$ is —CO—$C_{1-4}$-alkyl.

25. An isolated compound according to claim 1, wherein said compound is of Formula III and $R^{11}$ is —$CH_3$.

26. An isolated compound according to claim 1, wherein said compound is of Formula III and $R^{12}$ and $R^{13}$ are each independently —$CH_3$ or —$CH_2CH_3$.

27. An isolated compound according to claim 1, wherein X and Y are each O.

28. An isolated compound according to claim 1, wherein said compound is of Formula III and G is —$CH_2CH_2$—.

29. An isolated compound according to claim 1, wherein $R^3$ is H.

30. An isolated compound according to claim 1, wherein D is N—O.

31. An isolated compound according to claim 1, wherein:
each aryl group is, independently, a phenyl, naphthyl or biphenyl group optionally substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, or phenoxy;
each heteroaryl group is, independently, a furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, or benzoxazinyl group optionally substituted in one or more places by halogen, aryl, alkyl, alkoxy, carboxy, methylene, cyano, trifluoromethyl, nitro, oxo, amino, alkylamino, or dialkylamino; and
each heterocycle group is, independently, a heteroaryl group or a tetrahydrofuranyl, piperidinyl, or pyrrolidinyl group optionally substituted in one or more places by halogen, aryl, alkyl, alkoxy, carboxy, methylene, cyano, trifluoromethyl, nitro, oxo, amino, alkylamino, or dialkylamino.

32. An isolated compound according to claim 1, wherein $R^1$ is methyl or $CHF_2$; $R^2$ is alkyl, alkenyl, alkynyl, cycloalkyl, arylalkyl, heterocycle-alkyl, cycloalkylalkyl, aryl, or heterocyclic, in each case substituted or unsubstituted; and $R^3$ is aryl or heteroaryl, in each case substituted or unsubstituted.

33. An isolated compound according to claim 1, wherein $R^1$ is methyl or $CHF_2$; and $R^2$ is cyclopentyl, $CHF_2$, cyclopropylmethyl, pyridylethyl, or tetrahydrofuranyl.

34. An isolated compound according to claim 1, wherein $R^1$ is methyl or $CHF_2$; $R^2$ is cyclopentyl, $CHF_2$, cyclopropylmethyl, pyridylethyl, or tetrahydrofuranyl; and $R^3$ is aryl or heteroaryl, in each case substituted or unsubstituted.

35. An isolated compound according to claim 1, wherein $R^1$ is methyl or $CHF_2$; $R^2$ is cyclopentyl; and $R^3$ is substituted or unsubstituted aryl or heteroaryl.

36. An isolated compound according to claim 1, wherein $R^1$ is methyl; $R^2$ is cyclopentyl; and $R^3$ is phenyl which is substituted or unsubstituted.

37. An isolated compound according to claim 1, wherein $R^1$ is methyl; $R^2$ is cyclopentyl; and $R^3$ is phenyl or phenyl substituted with 1 to 3 substituents.

38. An isolated compound according to claim 1, wherein $R^1$ is methyl; $R^2$ is cyclopentyl; and $R^3$ is phenyl, naphthyl, biphenyl, pyridyl, pyrimidinyl, thiazolyl, pyrazinyl, quinolinyl, or isoquinolinyl, in each case substituted or unsubstituted.

39. An isolated compound according to claim 1, wherein $R^1$ is methyl or $CHF_2$.

40. An isolated compound according to claim 1, wherein $R^1$ is methyl or $CHF_2$, and B is N—O.

41. An isolated compound according to claim 1, wherein $R^1$ is methyl or $CHF_2$, and $R^2$ is cyclopentyl, $CHF_2$, cyclopropylmethyl, pyridylethyl, or tetrahydrofuranyl.

42. An isolated compound according to claim 1, wherein $R^1$ is methyl or $CHF_2$, B is N—O, and $R^2$ is cyclopentyl, $CHF_2$, cyclopropylmethyl, pyridylethyl, or tetrahydrofuranyl.

43. An isolated compound according to claim 1, wherein $R^1$ is methyl or $CHF_2$, and $R^3$ is 3-pyridyl or phenyl, which in each case is substituted or unsubstituted.

44. An isolated compound according to claim 1, wherein $R^1$ is methyl or $CHF_2$, B is N—O, and $R^3$ is 3-pyridyl or phenyl, which in each case is substituted or unsubstituted.

45. An isolated compound according to claim 1, wherein $R^1$ is methyl or $CHF_2$, $R^2$ is cyclopentyl, $CHF_2$, cyclopropylmethyl, pyridylethyl or tetrahydrofuranyl, and $R^3$ is 3-pyridyl or phenyl, which in each case is substituted or unsubstituted.

46. An isolated compound according to claim 1, wherein $R^1$ is methyl or $CHF_2$, B is N—O, $R^2$ is cyclopentyl, $CHF_2$, cyclopropylmethyl, pyridylethyl, or tetrahydrofuranyl, and $R^3$ is 3-pyridyl or phenyl, which in each case is substituted or unsubstituted.

47. An isolated compound according to claim 1, wherein $R^1$ is methyl or $CHF_2$, and $R^3$ is phenyl which is substituted in the 3- or 4-position.

48. An isolated compound according to claim 1, wherein $R^1$ is methyl or $CHF_2$, B is N—O, and $R^3$ is phenyl which is substituted in the 3- or 4-position.

49. An isolated compound according to claim 1, wherein $R^1$ is methyl or $CHF_2$, $R^2$ is cyclopentyl, $CHF_2$, cyclopropylmethyl, pyridylethyl, or tetrahydrofuranyl, and $R^3$ is phenyl which is substituted in the 3- or 4-position.

50. An isolated compound according to claim 1, wherein $R^1$ is methyl or $CHF_2$, B is N—O, $R^2$ is cyclopentyl, $CHF_2$, cyclopropylmethyl, pyridylethyl, or tetrahydrofuranyl, and $R^3$ is phenyl which is substituted in the 3- or 4-position.

51. An isolated compound according to claim 1, wherein $R^1$ is methyl or $CHF_2$, and $R^3$ is 3-pyridyl, 3-COOH-phenyl, 3-Cl-phenyl, 3-cyano-phenyl, 3- ethylsulfonamido-phenyl, 3-tetrazol-5-yl-phenyl, 3-hydroxymethyl-phenyl, 4-pyridyl, 4-COOH- phenyl, 4-cyano-phenyl, 4-ethylsulfonamido-phenyl, 4-tetrazol-5-yl-phenyl, or 4-hydroxymethyl- phenyl.

52. An isolated compound according to claim 1, wherein $R^1$ is methyl or $CHF_2$, B is N—O, and $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4- COOH-phenyl, 4-cyano-phenyl, 4-ethylsulfonamido-phenyl, 4-tetrazol-5-yl-phenyl, or 4-hydroxymethyl-phenyl.

53. An isolated compound according to claim 1, wherein $R^1$ is methyl or $CHF_2$, $R^2$ is cyclopentyl, $CHF_2$, cyclopropylmethyl, pyridylethyl, or tetrahydrofuranyl, and $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

54. An isolated compound according to claim 1, wherein $R^1$ is methyl or $CHF_2$, B is N—O, $R^2$ is cyclopentyl, $CHF_2$, cyclopropylmethyl, pyridylethyl, or tetrahydrofuranyl, and $R^3$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 3-nitro-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

55. An isolated compound according to claim 1, wherein $R^3$ is H or is aryl or heteroaryl, in each case substituted or unsubstituted.

56. An isolated compound according to claim 1, wherein said compound is of Formula II, $R^7$ is cycloalkyl; and $R^8$ is H or $C_2H_5$.

57. An isolated compound according to claim 1, wherein said compound is of Formula II, $R^7$ is cycloalkyl; $R^8$ is H or $C_2H_5$; and $R^3$ is H or is aryl or heteroaryl, in each case substituted or unsubstituted.

58. An isolated compound according to claim 1, wherein said compound is of Formula II, $R^7$ is cyclopentyl; $R^8$ is H or $C_2H_5$; and $R^3$ is H or is aryl or heteroaryl, in each case substituted or unsubstituted.

59. An isolated compound according to claim 1, wherein said compound is of Formula II, $R^7$ is cyclopentyl; $R^8$ is H or $C_2H_5$; and $R^3$ is phenyl which is substituted or unsubstituted.

60. An isolated compound according to claim 1, wherein $R^3$ is H or is aryl or heteroaryl, in each case substituted or unsubstituted.

61. An isolated compound according to claim 1, wherein said compound is of Formula III, $R^9$ is alkoxy having 1 to 4 carbon atoms; $R^{10}$ is $COCH_3$ or

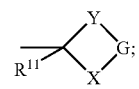

$R^{11}$ is —$CH_3$;

X and Y are both O or S; and

G is —$CH_2CH_2$—.

62. An isolated compound according to claim 1, wherein said compound is of Formula III, $R^3$ is H or is aryl or heteroaryl, in each case substituted or unsubstituted; $R^9$ is alkoxy having 1 to 4 carbon atoms;

$R^{10}$ is $COCH_3$ or

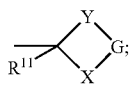

$R^{11}$ is —$CH_3$;
X and Y are both O or S; and
G is —$CH_2CH_2$—.

63. An isolated compound according to claim 1, wherein said compound is of Formula III and
$R^3$ is phenyl which is substituted or unsubstituted;
$R^9$ is alkoxy having 1 to 4 carbon atoms;
$R^{10}$ is $COCH_3$ or

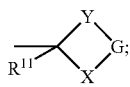

$R^{11}$ is —$CH_3$;
X and Y are both O or S; and
G is —$CH_2CH_2$—.

64. An isolated compound according to claim 1, wherein
B is N—O;
$R^1$ is methyl or difluoromethyl;
$R^2$ is phenyl, methylphenyl, methoxyphenyl, chlorophenyl, phenethyl, phenpropyl, phenbutyl, phenylethenyl, phenoxyethyl, phenoxypropyl, phenoxybutyl, chlorophenylethyl, methoxyphenylethyl, chlorophenylethenyl, chlorophenoxyethyl, chlorophenylpropyl, methoxyphenpropyl, methoxyphenbutyl, chlorophenbutyl, nitrophenbutyl, chlorophenylaminoethyl, cyclohexenyl, cyclohexadienyl, indan-2-yl methyl, difluoromethyl, trifluoromethyl, methoxyethyl, tetrahydrofuranyl, pyrrolidinyl, pyrrolyl, pyridylmethyl, pyridylethyl, pyridylpropyl, piperazinylmethyl, piperazinylethyl, methylpiperazinylethyl, cyclopentyl, $CHF_2$, methoxyethyl, cyclopropylmethyl, or phenylaminoethyl;
$R^3$ is phenyl or pyridyl, which in each case is unsubstituted or substituted;
$R^6$ is H or F;
$R^7$ is cyclopentyl, cyclohexyl, or alkyl having 2 to 4 carbon atoms which is optionally substituted by halogen,
$R^8$ H or $C_2H_5$;
$R^9$ is $CH_3$ or $C_2H_5$;
$R^{10}$ is —CO—$C_{1-4}$-alkyl;
$R^{11}$ is —$CH_3$;
$R^{12}$ and $R^{13}$ are each independently —$CH_3$ or —$CH_2CH_3$;
X and Y are each O; and
G is —$CH_2CH_2$—.

65. An isolated compound according to claim 1, wherein one of A, B and D is N—O and the others are CH;
$R^1$ is alkyl having 1 to 4 carbon atoms, which is branched or unbranched and which is unsubstituted or substituted one or more times by halogen;
$R^2$ is alkyl having 1 to 12 which is branched or unbranched and which is unsubstituted or substituted one or more times by halogen, hydroxy, cyano, $C_{1-4}$-alkoxy, oxo or combinations thereof, and wherein optionally one or more —$CH_2CH_2$— groups is replaced in each case by —CH=CH— or —C≡C—, cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof, cycloalkylalkyl having 4 to 16 carbon atoms which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, cyano, or combinations thereof, arylalkyl in which the aryl portion has 6 to 14 carbon atoms and the alkyl portion, which is branched or unbranched, has 1 to 5 carbon atoms, which the arylalkyl radical is unsubstituted or is substituted in the aryl portion one or more times by halogen, $CF_3$, $OCF_3$, alkyl, hydroxy, alkoxy, nitro, cyano, methylenedioxy, ethylenedioxy, or combinations thereof, and wherein in the alkyl portion one or more —$CH_2CH_2$— groups are each optionally replaced by —CH=CH— or —C≡C—, and one or more —$CH_2$— groups are each optionally replaced by —O— or —NH— and/or the alkyl portion is optionally substituted by halogen, oxo, hydroxy, cyano, or combinations thereof, a partially unsaturated carbocyclic group having 5 to 14 carbon atoms, which is unsubstituted or substituted one or more times by halogen, alkyl, alkoxy, hydroxy, nitro, cyano, oxo, or combinations thereof, a heterocyclic group, which is saturated, partially saturated or unsaturated, having 5 to 10 ring atoms in which at least 1 ring atom is a N, O or S atom, which is unsubstituted or substituted one or more times by halogen, hydroxy, aryl, alkyl, alkoxy, cyano, trifluoromethyl, nitro, oxo, or combinations thereof, or a heterocycle-alkyl group, wherein the heterocyclic portion is saturated, partially saturated or unsaturated, and has 5 to 10 ring atoms in which at least 1 ring atom is a N, O or S atom, and the alkyl portion is branched or unbranched and has 1 to 5 carbon atoms, the heterocycle-alkyl group is unsubstituted or substituted one or more times in the heterocyclic portion by halogen, $OCF_3$, hydroxy, aryl, alkyl, alkoxy, cyano, trifluoromethyl, nitro, oxo, or combinations thereof, wherein in the alkyl portion one or more —$CH_2CH_2$— groups are each optionally replaced by —CH=CH— or —C≡C—, and one or more —$CH_2$— groups are each optionally replaced by —O— or —NH— and/or the alkyl portion is optionally substituted by halogen, oxo, hydroxy, cyano, or combinations thereof;

$R^3$ is H,
aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof, or heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof;

$R^4$ is H,
alkyl having 1 to 8 carbon atoms, which is unsubstituted or substituted one or more times with halogen, $C_{1-4}$-alkyl, $C_{1-4}$-alkoxy, oxo, or combinations thereof,
alkylamino or dialkylamino wherein each alkyl portion has independently 1 to 8 carbon atoms,
a partially unsaturated carbocycle-alkyl group wherein the carbocyclic portion has 5 to 14 carbon atoms and the alkyl portion has 1 to 5 carbon atoms, which is unsubstituted or substituted, one or more times by halogen, alkyl, alkoxy, nitro, cyano, oxo, or combinations thereof,
cycloalkyl having 3 to 10 carbon atoms, which is unsubstituted or substituted one or more times by halogen, hydroxy, oxo, cyano, alkoxy, alkyl having 1 to 4 carbon atoms, or combinations thereof,
cycloalkylalkyl having 4 to 16 carbon atoms, which is unsubstituted or substituted in the cycloalkyl portion and/or the alkyl portion one or more times by halogen, oxo, cyano, hydroxy, alkyl, alkoxy or combinations thereof,
aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, or alkylsulfonyl,
arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, amino, alkylamino, or dialkylamino and/or substituted in the alkyl portion by halogen, cyano, or methyl,
a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or
a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof;

L is a single bond or a divalent aliphatic radical having 1 to 8 carbon atoms wherein one or more —$CH_2$— groups are each optionally replaced by —O—, —S—, —$NR^5$—, —$SO_2NH$—, —$NHSO_2$—, —CO—, —$NR^5CO$—, —$CONR^5$—, —NHCONH—, —OCONH, —NHCOO—, —SCONH—, —SCSNH—, or —NHCSNH—;

$R^5$ is H,
alkyl having 1 to 8 carbon atoms, which is branched or unbranched and which is unsubstituted or substituted one or more times with halogen, $C_{1-4}$-alkyl, $C_{1-4}$-alkoxy, oxo, or combinations thereof;

$R^7$ is H,
alkyl having 1 to 8 carbon atoms, which is branched or unbranched and which is unsubstituted or substituted one or more times by halogen,
cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof, or
a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof;

$R^8$ is H, or
alkyl having 1 to 4 carbon atoms, which is branched or unbranched and which is unsubstituted or substituted one or more times by halogen, cyano, and/or $C_{1-4}$-alkoxy, and one or more —$CH_2CH_2$— groups can be replaced in each case by —CH=CH— or —C≡C—;

$R^9$ is alkoxy or alkylthio, in each case having 1 to 4 carbon atoms, which is branched or unbranched and which is unsubstituted or substituted one or more times by halogen;

$R^{10}$ is —CO—$C_{1-4}$-alkyl which is branched or unbranched and which is unsubstituted or substituted one or more times by halogen, or is

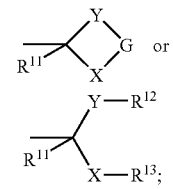

$R^{11}$ is H or alkyl having 1 to 4 carbon atoms, which is branched or unbranched, and which is unsubstituted or substituted one or more times by halogen;

$R^{12}$ is alkyl having 1 to 6 carbon atoms, which is branched or unbranched, and which is unsubstituted or substituted one or more times by halogen;

R[13] is alkyl having 1 to 6 carbon atoms, which is branched or unbranched, and which is unsubstituted or substituted one or more times by halogen;

X and Y are each independently O or S; and

G is alkylene having 2 to 7 carbon atoms which is unsubstituted or substituted one or more times by halogen.

66. An isolated compound according to claim 1, wherein said compound is selected from:

3'-Chloro-3-cyclopentyloxy-4-methoxy-N-(1-oxy-3-pyridylmethyl)diphenylamine,

3'-Chloro-4-methoxy-N-(1-oxy-3-pyridylmethyl)-3-(3-tetrahydrofuryloxy)diphenylamine, 3'-Cyano-4-methoxy-N-(1-oxy-3-pyridylmethyl)-3-((3R)-tetrahydrofuryloxy)diphenylamine, 4-Difluoromethoxy-N-(1-oxy-3-pyridylmethyl)-3-(3-tetrahydrofuryloxy)diphenylamine, 3,4-Bis(difluoromethoxy)-N-(1-oxy-3-pyridylmethyl)diphenylamine, 4-Difluoromethoxy-N-(1-oxy-3-pyridylmethyl)-3-((3R)-tetrahydrofuryloxy)diphenylamine, 3'-Cyano-4-difluoromethoxy-N-(1-oxy-3-pyridylmethyl)-3-((3R)-tetrahydrofuryloxy)diphenylamine, 3'-Chloro-4-difluoromethoxy-N-(1-oxy-3-pyridylmethyl)-3-((3R)-tetrahydrofuryloxy)diphenylamine, 4'-tert-Butyldimethylsilyloxy-3-cyclopentyloxy-4-methoxy-N-(1-oxy-3-pyridylmethyl)diphenylamine, N-(3-Cyclopentyloxy-4-methoxyphenyl)-N-(1-oxy-3-pyridylmethyl)-3-aminobenzoic acid, N-(3-Cyclopentyloxy-4-methoxyphenyl)-N-(1-oxy-3-pyridylmethyl)-4-aminobenzoic acid, N-(3-Cyclopentyloxy-4-difluoromethoxyphenyl)-N-(1-oxy-3-pyridylmethyl)-3-aminobenzoic acid, N-[4-Methoxy-3-(3-tetrahydrofuryloxy)phenyl]-N-(1-oxy-3-pyridylmethyl)-3-aminobenzoic acid, N-3,4-Bis(difluoromethoxy)phenyl-N-(1-oxy-3-pyridylmethyl)-3-aminobenzoic acid, N-[4-methoxy-3-((3R)-tetrahydrofuryloxy)phenyl]-N-(1-oxy-3-pyridylmethyl)-3-aminobenzoic acid, N-(3-Cyclopropylmethoxy-4-methoxyphenyl)-N-(1-oxy-3-pyridylmethyl)-4-aminobenzoic acid, N-(3-Cyclopropylmethoxy-4-difluoromethoxyphenyl)-N-(1-oxy-3-pyridylmethyl)-3-aminobenzoic acid, N-[3-(4-Chlorophenyl)prop-1-yloxy-4-methoxyphenyl]-N-(1-oxy-3-pyridylmethyl)-3-aminobenzoic acid, N-(3-Cyclopropylmethoxy-4-methoxyphenyl)-N-(1-oxy-3-pyridylmethyl)-3-aminobenzoic acid, N-[3-(2-Indanyloxy)-4-methoxyphenyl]-N-(1-oxy-3-pyridylmethyl)-3-aminobenzoic acid, N-[4-Methoxy-3-(3-tetrahydrofuryloxy)phenyl]-N-(1-oxy-3-pyridylmethyl)-3-aminobenzoic acid, N-[4-Methoxy-3-((3R)-tetrahydrofuryloxy)phenyl]-N-(1-oxy-3-pyridylmethyl)-3-aminobenzoic acid, N-[3-(2-Methoxyethoxy)-4-methoxyphenyl]-N-(1-oxy-3-pyridylmethyl)-3-aminobenzoic acid, 3-Cyclopropylmethyloxy-4-difluoromethoxy-N-(1-oxy-3-pyridylmethyl)-4'-(2H-tetrazol-5-yl)diphenylamine, 3-Cyclopentyloxy-4-methoxy-N-(1-oxy-3-pyridylmethyl)-4'-(2H-tetrazol-5-yl)diphenylamine, 3-Cyclopentyloxy-4-methoxy-N-(1-oxy-3-pyridylmethyl)-3'-(2H-tetrazol-5-yl)diphenylamine, 4-Methoxy-N-(1-oxy-3-pyridylmethyl)-3-((3R)-tetrahydrofuryloxy)-4'-(2H-tetrazol-5-yl)diphenylamine, 3-Cyclopropylmethyloxy-4-methoxy-N-(1-oxy-3-pyridylmethyl)-4'-(2H-tetrazol-5-yl)diphenylamine, 4-Difluoromethoxy-N-(1-oxy-3-pyridylmethyl)-3-((3R)-tetrahydrofuryloxy)-4'-(2H-tetrazol-5-yl)diphenylamine, 3-Cyclopentyloxy-4-difluoromethoxy-N-(1-oxy-3-pyridylmethyl)-4'-(2H-tetrazol-5-yl)diphenylamine, 3-Cyclopropylmethyloxy-4-difluoromethoxy-N-(1-oxy-3-pyridylmethyl)-3'-(2H-tetrazol-5-yl)diphenylamine, Bis-3,4-difluoromethoxy-N-(1-oxy-3-pyridylmethyl)-4'-(2H-tetrazol-5-yl)diphenylamine, N-(3-Cyclopentyloxy-4-methoxyphenyl)-N-(3-pyridyl)-N-(1-oxy-3-pyridylmethyl)amine, N-(3-Cyclopentyloxy-4-difluoromethoxyphenyl)-N-(3-pyridyl)-N-(1-oxy-3-pyridylmethyl)amine, N-(3-Cyclopropylmethoxy-4-difluoromethoxyphenyl)-N-(3-pyridyl)-N-(1-oxy-3-pyridylmethyl)amine, N-(4-Difluoromethoxy-3-(3R)-tetrahydrofuryloxyphenyl)-N-(3-pyridyl)-N-(1-oxy-3-pyridylmethyl)amine, 3-Cyclopentyloxy-3'-ethanesulfonylamino-4-methoxy-N-(1-oxy-3-pyridylmethyl)diphenylamine, 3-Cyclopentyloxy-4-methoxy-3'-(1-propanesulfonylamino)-N-(1-oxy-3-pyridylmethyl)diphenylamine, 3-Cyclopentyloxy-4'-ethanesulfonylamino-4-methoxy-N-(1-oxy-3-pyridylmethyl)diphenylamine, 3-Cyclopentyloxy-4-methoxy-4'-(1-propanesulfonylamino)-N-(1-oxy-3-pyridylmethyl)diphenylamine, 3-Cyclopropylmethoxy-3'-ethanesulfonylamino-4-methoxy-N-(1-oxy-3-pyridylmethyl)diphenylamine, 4-Difluoromethoxy-3'-ethanesulfonylamino-N-(1-oxy-3-pyridylmethyl)-3-[(3R)-tetrahydrofuryloxy]diphenylamine, 4-Methoxy-3-[2-(2-pyridyl)ethoxy]-N-(1-oxy-3-pyridylmethyl)diphenylamine, 4-Methoxy-N-(1-oxy-3-pyridylmethyl)-3-[(3R)-tetrahydrofuryloxy]diphenylamine, 3'-Chloro-4-methoxy-3-[2-(2-pyridyl)ethoxy]-N-(1-oxy-3-pyridylmethyl)diphenylamine, 3'-Chloro-4-methoxy-N-(1-oxy-3-pyridylmethyl)-3-[(3R)-tetrahydrofuryloxy]diphenylamine, 3-Cyclopentyloxy-4-methoxy-4'-[2-(5-oxopyrrolidinyl)methoxy]-N-(1-oxy-3-pyridylmethyl)diphenylamine, 3-Cyclopentyloxy-4-methoxy-N-(3-aminocarbonylphenyl)-N-(1-oxy-3-pyridylmethyl)aniline, 3,4-Bisdifluoromethoxy-N-(3-carboxy-4-chlorophenyl)-N-(1-oxy-3-pyridylmethyl)aniline, 3,4-Bisdifluoromethoxy-N-(4-(1-pyrrol-1-yl)phenyl)-N-(1-oxy-3-pyridylmethyl)aniline, 4-Methoxy-3-(R)-tetrahydrofuryloxy-N-(3-carboxy-4-chlorophenyl)-N-(1-oxy-3-pyridylmethyl)aniline, 4-Methoxy-3-(R)-tetrahydrofuryloxy-N-(3-carboxyphenyl)-N-(1-oxy-4-pyridylmethyl)aniline, 4-Methoxy-3-(R)-tetrahydrofuryloxy-N-(3-pyridyl)-N-(1-oxy-4-pyridylmethyl)aniline, 3-Cyclopentyloxy-4-methoxy-N-(4-carboxy-3-chlorophenyl)-N-(1-oxy-3-pyridylmethyl)aniline, 2-Acetyl-7-methoxy-4-(N-(4-cyanophenyl)-N-(1-oxy-3-pyridylmethyl))aminobenzofuran, 2-Acetyl-7-methoxy-4-(N-phenyl-N-(1-oxy-4-pyridylmethyl))aminobenzofuran, 2-Acetyl-7-methoxy-4-(N-(3-carboxyphenyl)-N-(1-oxy-3-pyridylmethyl))aminobenzofuran, 1-Cyclopentyl-3-ethyl-6-(N-(3-carboxyphenyl)-N-(1-oxy-3-pyridylmethyl))aminoindazole, 2-Acetyl-7-methoxy-4-(N-(4-acetylphenyl)-N-(1-oxy-3-pyridylmethyl))aminobenzofuran, N-[4-Methoxy-3-((3R)-3-tetrahydrofuranyl)oxyphenyl]-4-methylsulfonylaminocarbonyl-N-(1-oxy-3-pyridylmethyl)aniline, 4-(4-Fluorophenyl)sulfonylaminocarbonyl-N-[4-methoxy-3-((3R)-3-tetrahydrofuranyl)oxyphenyl]-N-(1-oxy-3-pyridylmethyl)aniline, 3-Chloro-N-[4-methoxy-3-((3R)-3-tetrahydrofuranyl)oxyphenyl]-N-(1-oxy-3-pyridylmethyl)aniline, 3-Amino-N-(5-fluoro-1-oxy-3-pyridylmethyl)-N-(4-methoxy-3-((3R)-3-tetrahydrofuranyl)oxyphenyl]benzoic acid, 3-Amino-N-(3-cyclopentyloxy-4-methoxyphenyl)-N-(1-oxy-2-pyridylmethyl)benzoic acid, 3-Amino-N-[4-methoxy-3-((3R)-3-tetrahydrofuranyl)oxyphenyl]-N-(1-oxy-3-pyridylmethyl)-5-trifluoromethylbenzoic acid, 4-Ethylsulfonylaminocarbonyl-N-[4-methoxy-3-((3R)-3-tetrahydrofuranyl)oxyphenyl]-N-(1-oxy-3-pyridylmethyl)aniline, 4-(2-Fluorophenyl)sulfonylaminocarbonyl-N-[4-methoxy-3-((3R)-3-tetrahydrofuranyl)oxyphenyl]-N-(1-oxy-3-pyridylmethyl)aniline 4-(3-Chlorophenyl)sulfonylaminocarbonyl-N-[4-methoxy-3-((3R)-3-tetrahydrofuranyl)oxyphenyl]-N-(1-oxy-3-pyridylmethyl)aniline, 3-Amino-N-[4-methoxy-3-((3R)-3-tetrahydrofuranyl)oxyphenyl]-N-(1-oxy-3-pyridylmethyl)-6-trifluoromethylbenzoic acid, 4-Amino-N-[4-difluoromethoxy-3-((3R)-3-tetrahydrofuranyl)oxyphenyl]-N-(1-oxy-3-pyridylmethyl)benzoic acid, N-[4-Difluoromethoxy-3-((3R)-3-tetrahydrofuranyl)oxyphenyl]-4-methylsulfonylaminocarbonyl-N-(1-oxy-3-pyridylmethyl)aniline, N-[4-Methoxy-3-((3R)-3-tetrahydrofuranyl)oxyphenyl]-N-(1-oxy-3-pyridylmethyl)-4-phenylsulfonylaminocarbonylaniline, 3-Amino-N-(3-cyclopentyloxy-4-methoxyphenyl)-N-(5-fluoro-1-oxy-3-pyridylmethyl)benzoic acid, 4-Amino-N-(3-cyclopentyloxy-4-methoxyphenyl)-N-(5-fluoro-1-oxy-3-pyridylmethyl)benzoic acid, 3-Amino-N-[4-difluoromethoxy-3-((3R)-3-tetrahydrofuranyl)oxyphenyl]-N-(1-oxy-3-pyridylmethyl)benzoic acid, 3-Amino-N-(3-cyclobutyloxy-4-methoxyphenyl)-N-(1-oxy-3-pyridylmethyl)benzoic acid, 3-Amino-N-(3-cyclopentyloxy-4-methoxyphenyl)-5-fluoro-N-(1-oxy-3-pyridylmethyl)benzoic acid, 3-Amino-N-[3,4-bis(difluoromethoxy)phenyl]-5-fluoro-N-(1-oxy-3-pyridylmethyl)benzoic acid, 4-Amino-N-(3-cyclobutyloxy-4-methoxyphenyl)-N-(1-oxy-3-pyridylmethyl)benzoic acid, 4-Amino-N-(3-ethoxy-4-methoxyphenyl)-N-(1-oxy-3-pyridylmethyl)benzoic acid, 4-Amino-N-(3-isopropoxy-4-methoxyphenyl)-N-(1-oxy-3-pyridylmethyl)benzoic acid, N-[4-Difluoromethoxy-3-((3R)-3-tetrahydrofuranyl)oxyphenyl]-4-(3,4-difluorophenyl)sulfonylaminocarbonyl-N-(1-oxy-3-pyridylmethyl)aniline, 4-Amino-N-(3-cyclopropylmethoxy-4-methoxyphenyl)-N-(1-oxy-3-pyridylmethyl)benzoic acid, N-[3,4-Bis(difluoromethoxy)phenyl]-4-(4-fluorophenyl)sulfonylaminocarbonyl-N-(1-oxy-3-pyridylmethyl)aniline, 4-(2,4-Difluorophenyl)sulfonylaminocarbonyl-N-[4-methoxy-3-((3R)-3-tetrahydrofuranyl)oxyphenyl]-N-(1-oxy-3-pyridylmethyl)aniline, 4-(3,4-Difluorophenyl)sulfonylaminocarbonyl-N-[4-methoxy-3-((3R)-3-tetrahydrofuranyl)oxyphenyl]-N-(1-oxy-3-pyridylmethyl)aniline, N-[4-Difluoromethoxy-3-((3R)-3-tetrahydrofuranyl)oxyphenyl]-4-ethylsulfonylaminocarbonyl-N-(1-oxy-3-pyridylmethyl)aniline, 3-Amino-N-(3,4-dimethoxyphenyl)-N-(1-oxy-3-pyridylmethyl)benzoic acid, 3-Amino-N-(3-ethoxy-4-methoxyphenyl)-N-(1-oxy-3-pyridylmethyl)benzoic acid, 3-Amino-N-(3-isopropoxy-4-methoxyphenyl)-N-(1-oxy-3-pyridylmethyl)benzoic acid, 4-(3,4-Difluorophenyl)sulfonylaminocarbonyl-N-(3-ethoxy-4-methoxyphenyl)-N-(1-oxy-3-pyridylmethyl)aniline, 3-Amino-N-[3,4-bis(difluoromethoxy)phenyl]-N-(1-oxy-3-pyridylmethyl)benzoic acid, 3-Amino-N-(4-difluoromethoxy-3-ethoxyphenyl)-N-(1-oxy-3-pyridylmethyl)benzoic acid, 4-Amino-N-(4-difluoromethoxy-3-ethoxyphenyl)-N-(1-oxy-3-pyridylmethyl)benzoic acid, 3-Amino-N-(4-difluoromethoxy-3-methoxyphenyl)-N-(1-oxy-3-pyridylmethyl)benzoic acid, 4-Amino-N-(3-cyclopentyloxy-4-methoxyphenyl)-N-(1-oxypyridin-3-ylmethyl)pyridine, N-[Bis-3,4-(difluoromethoxy)phenyl]-N-(1-oxy-3-pyridylmethyl)-4-[2-(2-tetrahydropyranyl)-2H-tetrazol-5-yl]aniline, N-[Bis-3,4-(difluoromethoxy)phenyl]-N-(1-oxy-3-pyridylmethyl)-3-(2H-tetrazol-5-yl)aniline; and pharmaceutically acceptable salts thereof, wherein optically active compounds can be in the form of their separate enantiomers or mixtures thereof, including racemic mixtures.

67. An isolated compound according to claim 1, wherein said compound is selected from:

4-amino-N-(3-cyclopentyloxy-4-methoxyphenyl)-N-(1-oxypyridin-3-ylmethyl)pyridine, N-[Bis-3,4-(difluoromethoxy)phenyl]-N-(1-oxy-3-pyridylmethyl)-4-[2-(2-tetrahydropyranyl)-2H-tetrazol-5-yl]aniline, 3-Chloro-N-[4-methoxy-3-((3R)-3-tetrahydrofuranyl)oxyphenyl]-N-(1-oxy-3-pyridylmethyl)aniline, 4-Amino-N-(3-cyclopentyloxy-4-methoxyphenyl)-N-(1-oxy-3-pyridylmethyl)benzoic acid, 3-Amino-N-(3-cyclopentyloxy-4-methoxyphenyl)-N-(1-oxy-3-pyridylmethyl)benzoic acid, 3-Amino-N-[bis-3,4-(difluoromethoxy)phenyl]-N-(1-oxy-3-pyridylmethyl)benzoic acid, N-[Bis-3,4-(difluoromethoxy)phenyl]-N-(1-oxy-3-pyridylmethyl)-3-(2H-tetrazol-5-yl)aniline; and pharmaceutically acceptable salts thereof, wherein optically active compounds can be in the form of their separate enantiomers or mixtures thereof, including racemic mixtures.

68. A pharmaceutical composition containing a pharmaceutically acceptable carrier and a compound of Formulas I–III:

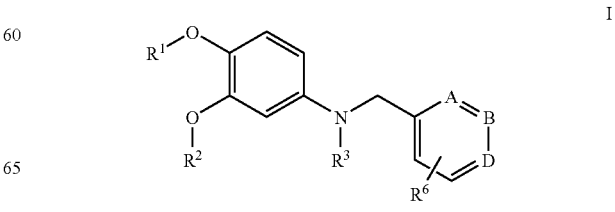

-continued

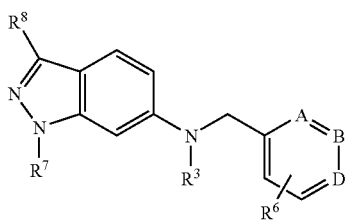

II

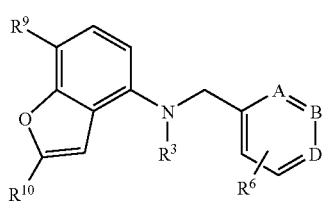

III wherein
one of A, B and D is N—O and the others are $CR^6$;
  $R^1$ is alkyl having 1 to 4 carbon atoms, which is branched or unbranched and which is unsubstituted or substituted one or more times by halogen;
  $R^2$ is alkyl having 1 to 12 carbon atoms which is branched or unbranched and which is unsubstituted or substituted one or more times by halogen, hydroxy, cyano, $C_{1-4}$-alkoxy, oxo or combinations thereof, and wherein optionally one or more —$CH_2CH_2$— groups is replaced in each case by —CH=CH— or —C≡C—,
    cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof,
    cycloalkylalkyl having 4 to 16 carbon atoms which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof,
    aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, cyano, or combinations thereof,
    arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, $CF_3$, $OCF_3$, alkyl, hydroxy, alkoxy, nitro, cyano, methylenedioxy, ethylenedioxy, or combinations thereof, and wherein in the alkyl portion one or more —$CH_2CH_2$— groups are each optionally replaced by —CH=CH— or —C≡C—, and/or one or more —$CH_2$— groups are each optionally replaced by —O— or —NH— and/or the alkyl portion is optionally substituted by halogen, oxo, hydroxy, cyano, or combinations thereof,
    a partially unsaturated carbocyclic group having 5 to 14 carbon atoms, which is unsubstituted or substituted one or more times by halogen, alkyl, alkoxy, hydroxy, nitro, cyano, oxo, or combinations thereof,
    a heterocyclic group, which is saturated, partially saturated or unsaturated, having 5 to 10 ring atoms in which at least 1 ring atom is an N, O or S atom, wherein the heterocyclic group is unsubstituted or substituted one or more times by halogen, hydroxy, aryl, alkyl, alkoxy, cyano, trifluoromethyl, nitro, oxo, or combinations thereof, or
    a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted or substituted one or more times in the heterocyclic portion by halogen, $OCF_3$, hydroxy, aryl, alkyl, alkoxy, cyano, trifluoromethyl, nitro, oxo, or combinations thereof, wherein in the alkyl portion one or more —$CH_2CH_2$— groups are each optionally replaced by —CH=CH— or —C≡C—, and/or one or more —$CH_2$— groups are each optionally replaced by —O— or —NH— and/or the alkyl portion is optionally substituted by halogen, oxo, hydroxy, cyano, or combinations thereof;
  $R^3$ is H,
    cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof,
    aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, pyrrolyl, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof,
    heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^4$-L-, or combinations thereof, or
    a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, trifluoromethyl, nitro, oxo, or combinations thereof;
  $R^4$ is H,
    alkyl having 1 to 8 carbon atoms which is unsubstituted or substituted one or more times by halogen, $C_{1-4}$-alkyl, $C_{1-4}$-alkoxy, oxo, or combinations thereof,
    alkylamino or dialkylamino wherein each alkyl portion has independently 1 to 8 carbon atoms,
    a partially unsaturated carbocycle-alkyl group wherein the carbocyclic portion has 5 to 14 carbon atoms and the alkyl portion has 1 to 5 carbon atoms, which is unsubstituted or substituted one or more times by halogen, alkyl, alkoxy, nitro, cyano, oxo, or combinations thereof, cycloalkyl having 3 to 10 carbon atoms which is unsubstituted or substituted one or more times by halogen, hydroxy, oxo, cyano, alkoxy, alkyl having 1 to 4 carbon atoms, or combinations thereof, cycloalkylalkyl having 4 to 16 carbon atoms which is unsubstituted or substituted in the cycloalkyl portion and/or the alkyl portion one or more times by halogen, oxo, cyano, hydroxy, alkyl, alkoxy or combinations thereof, aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy, dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, cycloalkyl, aryl, heteroaryl, or combinations thereof, arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH═CH— or —C≡C—, and/or one or more —CH$_2$— groups are each optionally replaced by —O— or —NH—, a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or a heterocycle-alkyl group, wherein the heterocycle portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, CF$_3$O, nitro, oxo, amino, alkylamino, dialkylamino, or combinations thereof and/or substituted in the alkyl portion by halogen, cyano, or methyl or combinations thereof;

L is a single bond or a divalent aliphatic radical having 1 to 8 carbon atoms wherein one or more —CH$_2$— groups are each optionally replaced by —O—, —S—, —SO—, —SO$_2$—, —NR$^5$—, —SO$_2$NH—, —NHSO$_2$—, —SO$_2$NR$^5$—, —NR$^5$SO$_2$—, —CO—, —NR$^5$CO—, —CONR$^5$—, —NHCONH—, —OCONH—, —NHCOO—, —SCONH—, —SCSNH—, or —NHCSNH—;

R$^5$ is H,
alkyl having 1 to 8 carbon atoms, which is branched or unbranched and which is unsubstituted or substituted one or more times by halogen, C$_{1-4}$-alkyl, C$_{1-4}$-alkoxy, oxo, or combinations thereof, aryl having 6 to 14 carbon atoms and which is unsubstituted or substituted one or more times by halogen, alkyl, hydroxy, alkoxy, alkoxyalkoxy, nitro, ethylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, or combinations thereof, or arylalkyl having 7 to 19 carbon atoms, wherein the aryl portion has 6 to 14 carbon atoms and the alkyl portion, which is branched or unbranched, has 1 to 5 carbon atoms, wherein the arylalkyl radical is unsubstituted or substituted, in the aryl portion, one or more times by halogen, trifluoromethyl, CF$_3$O, nitro, amino, alkyl, alkoxy, amino, alkylamino, dialkylamino, or combinations thereof, and/or substituted in the alkyl portion by halogen, cyano, methyl, or combinations thereof, wherein in the alkyl portion one or more —CH$_2$CH$_2$— groups are each optionally replaced by —CH═CH— or —C≡C—, and/or one or more —CH$_2$— groups are each optionally replaced by —O— or —NH—;

R$^6$ is H, halogen, alkyl having 1 to 4 carbon atoms, alkoxy having 1 to 4 carbon atoms, CN, or hydroxyl;

R$^7$ is H,
alkyl having 1 to 8 carbon atoms, which is branched or unbranched and which is unsubstituted or substituted one or more times by halogen, cyano, hydroxy, C$_{1-4}$-alkoxy, or combinations thereof cycloalkyl having 3 to 10 carbon atoms which is unsubstituted or substituted one or more times by halogen, hydroxy, oxo, cyano, alkyl having 1 to 4 carbon atoms, alkoxy having 1 to 4 carbon atoms, or combinations thereof, cycloalkylalkyl having 4 to 16 carbon atoms which is unsubstituted or substituted in the cycloalkyl portion and/or the alkyl portion one or more times by halogen, oxo, cyano, hydroxy, C$_{1-4}$-alkyl, C$_{1-4}$-alkoxy or combinations thereof, aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, cyano, or combinations thereof, arylalkyl in which the aryl portion has 6 to 14 carbon atoms and the alkyl portion, which is branched or unbranched, has 1 to 5 carbon atoms, wherein the arylalkyl radical is unsubstituted or is substituted in the aryl portion one or more times by halogen, CF$_3$, OCF$_3$, alkyl, hydroxy, alkoxy, nitro, cyano, methylenedioxy, ethylenedioxy, or combinations thereof, and wherein in the alkyl portion one or more —CH$_2$CH$_2$— groups are each optionally replaced by —CH═CH— or —C≡C—, and/or one or more —CH$_2$— groups are each optionally replaced by —O— or —NH— and/or the alkyl portion is optionally substituted by halogen, oxo, hydroxy, cyano, or combinations thereof, a heterocyclic group, which is saturated, partially saturated or unsaturated, having 5 to 10 ring atoms in which at least 1 ring atom is an N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or
a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof;

$R^8$ is H, or
alkyl having 1 to 4 carbon atoms, which is branched or unbranched and which is unsubstituted or substituted one or more times by halogen, cyano, and/or $C_{1-4}$-alkoxy, and one or more —$CH_2CH_2$— groups can be replaced in each case by —CH=CH— or —C≡C—;

$R^9$ is alkoxy or alkylthio, in each case having 1 to 4 carbon atoms, which is branched or unbranched and which is unsubstituted or substituted one or more times by halogen;

$R^{10}$ is —CO—$C_{1-4}$-alkyl which is branched or unbranched and which is unsubstituted or substituted one or more times by halogen, or is

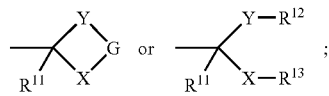

$R^{11}$ is H or alkyl having 1 to 4 carbon atoms, which is branched or unbranched, and which is unsubstituted or substituted one or more times by halogen;

$R^{12}$ is alkyl having 1 to 6 carbon atoms, which is branched or unbranched, and which is unsubstituted or substituted one or more times by halogen;

$R^{13}$ is alkyl having 1 to 6 carbon atoms, which is branched or unbranched, and which is unsubstituted or substituted one or more times by halogen;

X and Y are each independently O or S; and

G is alkylene having 2 to 7 carbon atoms which is unsubstituted or substituted one or more times by halogen; or a pharmaceutically acceptable salt thereof;
wherein an optically active compound can be in the form of one of its separate enantiomers or mixtures thereof, including racemic mixtures.

69. A composition of claim 68, wherein the compound is provided in a unit dosage of 0.1–50 mg.

70. A method for enhancing cognition and/or treating psychosis in a patient comprising administering to said patient an effective amount of a composition according to claim 68.

71. A method according to claim 70, wherein said compound is administered in an amount of 0.01–100 mg/kg of body weight/day.

72. A method according to claim 70, wherein said patient is a human.

73. A method of claim 70, wherein the patient is suffering from cognition impairment or decline.

74. A method according to claim 70, wherein said patient is suffering from memory impairment.

75. A method according to claim 74, wherein said patient is suffering from memory impairment due to Alzheimer's disease, multiple sclerosis, amylolaterosclerosis, multiple systems atrophy, schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia, an acute neuronal disease, HIV, cardiovascular disease, or age-related cognitive decline.

76. A method according to claim 74, wherein said patient is suffering from memory impairment due to dementia.

77. A method according to claim 70, wherein said patient is suffering from a psychosis.

78. A method according to claim 77, wherein the psychosis is schizophrenia, bipolar or manic depression, or major depression.

79. A method according to claim 70, wherein the patient is treated to effect PDE4 enzyme inhibition.

80. A method of treating a patient suffering from an allergic or inflammatory disease comprising administering to said patient an effective amount of a composition according to claim 68.

81. A method of treating a patient suffering from neurodegeneration resulting from a disease or injury comprising administering to said patient an effective amount of a composition according to claim 68.

82. The method of claim 81, wherein the disease or injury is stroke, spinal cord injury, Alzheimer's disease, multiple sclerosis, amylolaterosclerosis (ALS), or multiple systems atrophy (MSA).

83. An isolated compound according to claim 1, wherein said compound is in the form of a substantially pure enantiomer.

84. A method for treating drug addiction or morphine dependence in a patient comprising administering to said patient an effective amount of a composition according to claim 68.

* * * * *

UNITED STATES PATENT AND TRADEMARK OFFICE
CERTIFICATE OF CORRECTION

PATENT NO. : 7,087,625 B2  
APPLICATION NO. : 10/715819  
DATED : August 8, 2006  
INVENTOR(S) : Allen T. Hopper It is certified that error appears in the above-identified patent and that said Letters Patent is hereby corrected as shown below:

Title Page, In Abstract, in the Second Formula, the first "$R^6$" should read -- $R^8$ --  
Title Page, In Abstract, after the Second Formula, insert the designation -- II --  
Column 3, line 23, in the Second Formula, the first "$R^6$" should read -- $R^8$ --  
Column 3, line 23, after the Second Formula, insert the designation -- II --  
Column 34, line 13, in the Second Formula, the first "$R^6$" should read -- $R^8$ --  
Column 34, line 13, after the Second Formula, insert the designation -- II --  
Column 36, line 59, reads "is a N, O or S" should read -- is an N, O or S --  
Column 37, line 4, reads "—$SO_2$—,—$NR^5$—," should read -- —$SO_2$—, —$NR^5$—, --  
Column 37, lines 5-6, reads "—CO—,—$NR^5$CO—;" should read  
  -- —CO—,—$NR^5$CO—, --  
Column 37, line 6, reads "—$CONR^5$—,—NHCONH—;" should read-- —$CONR^5$—,  
  —NHCONH—, --  
Column 37, line 6, reads "—OCONH," should read -- —OCONH—, --  
Column 37, lines 16-17, reads "ethylenedioxy, ethylenedioxy," should read  
  -- methylenedioxy, ethylenedioxy, --  
Column 37, line 43, reads "or combinations thereof" should read -- or combinations  
  thereof, --  
Column 39, line 32, reads "and $R^2$ cyclopentyl," should read -- and $R^2$ is cyclopentyl, --  
Column 40, line 17, reads "$R^8$ H" should read -- $R^8$ is H --  
Column 43, line 49, reads "$R^8$ H" should read -- $R^8$ is H --  
Column 44, line 18, reads "carbon atoms, which" should read -- carbon atoms, in  
  which --  
Column 44, line 37, reads "is a N, O or S" should read -- is an N, O or S --  
Column 44, line 54, reads "—O —or" should read -- —O — or --  
Column 45, line 6, reads "aminoalkoxy dialkylamino," should read -- aminoalkoxy,  
  dialkylamino, --  
Column 45, lines 37-38, reads "aminoalkoxy dialkylamino," should read  
  -- aminoalkoxy, dialkylamino, --  
Column 45, line 47, reads "alkylamino,or" should read -- alkylamino, or --  
Column 45, lines 55-56, reads "aminoalkoxy dialkylamino," should read  
  -- aminoalkoxy, dialkylamino, --  
Column 45, line 64, reads "is a N, O or S" should read -- is an N, O or S --  
Column 46, line 11, reads "—OCONH," should read -- —OCONH—, --  
Column 46, lines 33-34, reads "aminoalkoxy dialkylamino," should read  
  -- aminoalkoxy, dialkylamino, --  
Column 52, lines 32-33, reads "aminoalkoxy dialkylamino," should read  
  -- aminoalkoxy, dialkylamino, --  
Column 52, line 44, reads "aminoalkoxy dialkylamino," should read -- aminoalkoxy,  
  dialkylamino, --

UNITED STATES PATENT AND TRADEMARK OFFICE
CERTIFICATE OF CORRECTION

PATENT NO. : 7,087,625 B2
APPLICATION NO. : 10/715819
DATED : August 8, 2006
INVENTOR(S) : Allen T. Hopper It is certified that error appears in the above-identified patent and that said Letters Patent is hereby corrected as shown below:

Column 53, lines 39-40, reads "aminoalkoxy dialkylamino," should read
-- aminoalkoxy, dialkylamino, --
Column 53, lines 50-51, delete line break between "or" and "substituted"
Column 54, lines 5-6, reads "ethylenedioxy, ethylenedioxy," should read
-- methylenedioxy, ethylenedioxy, --
Column 54, lines 7-8, reads "aminoalkoxy dialkylamino," should read -- aminoalkoxy, dialkylamino, --
Column 54, line 32, reads "or combinations thereof" should read -- or combinations thereof, --
Column 55, lines 1-2, reads "aminoalkoxy dialkylamino," should read -- aminoalkoxy, dialkylamino, --
Column 55, line 17, reads "or methyl or" should read -- or methyl, or --

Signed and Sealed this

Tenth Day of November, 2009

David J. Kappos
*Director of the United States Patent and Trademark Office*